(12) United States Patent
Leonardi et al.

(10) Patent No.: US 6,306,861 B1
(45) Date of Patent: Oct. 23, 2001

(54) THIENOPYRANCECARBOXAMIDE DERIVATIVES

(75) Inventors: Amedeo Leonardi, Milan; Gianni Motta, Barlassina; Carlo Riva, Varese; Rodolfo Testa, Vignate, all of (IT)

(73) Assignee: Recordati S.A. Chemical and Pharmaceutical Company, Chiasso (CH)

( * ) Notice: Subject to any disclaimer, the term of this patent is extended or adjusted under 35 U.S.C. 154(b) by 0 days.

(21) Appl. No.: 09/627,766

(22) Filed: Jul. 28, 2000

Related U.S. Application Data

(60) Provisional application No. 60/179,423, filed on Jan. 31, 2000.

(30) Foreign Application Priority Data

Jul. 30, 1999 (IT) .............................................. MI99A1704

(51) Int. Cl.⁷ ........................ C07D 405/12; A61K 31/496
(52) U.S. Cl. ....................... 514/254.11; 544/377
(58) Field of Search ........................ 544/377; 514/254.11

(56) References Cited

U.S. PATENT DOCUMENTS 4,089,969   5/1978  Muchowski et al. ................ 424/274

(List continued on next page.)

FOREIGN PATENT DOCUMENTS 0 558 245 A1   9/1993  (EP) ............................. C07D/311/30

(List continued on next page.)

OTHER PUBLICATIONS

Albertson, Noel F., "Synthesis of Peptides With Mixed Anhydrides"; *Organic Reactions*; 12: 204–218 (1962).

(List continued on next page.)

*Primary Examiner*—Mukund J. Shah
*Assistant Examiner*—Hong Liu
(74) *Attorney, Agent, or Firm*—Darby & Darby

(57) ABSTRACT

The invention is directed to compounds of Formula I:

(I)

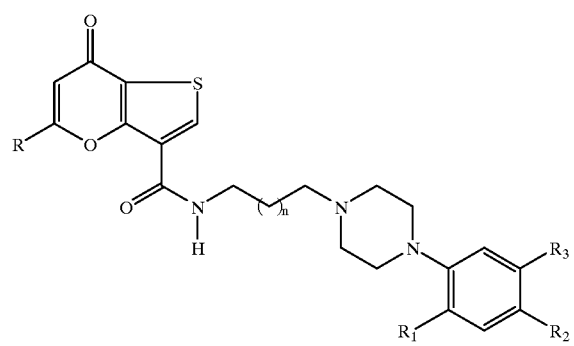

wherein

R is an aryl, cycloalkyl or polyhaloalkyl group, $R_1$ is chosen from the group consisting of alkyl, alkoxy, polyfluoroalkoxy, hydroxy and trifluoromethanesulfonyloxy; each of $R_2$ and $R_3$ independently is chosen from the group consisting of a hydrogen, halogen, alkoxy and polyfluoroalkoxy group, and n is 0, 1 or 2.

The invention further provides pharmaceutical compositions comprising a compound of Formula I or a N-oxide or pharmaceutically acceptable salt of such a compound in admixture with a pharmaceutically acceptable diluent or carrier.

In another aspect, the present invention is directed to methods for selectively preventing contractions of the urethra and lower urinary tract, without substantially affecting blood pressure, by administering one or more selected compounds of Formula I to a mammal (including a human) in need of such treatment in an amount or amounts effective for the particular use.

In yet another aspect, the invention is directed to methods for blocking $\alpha_1$ receptors, by delivering to the environment of said receptors, e.g., to the extracellular medium, (or by administering to a mammal possessing said receptors) an effective amount of a compound of the invention, in this way relieving diseases associated to overactivity of said receptors.

It is also an object of the present invention to provide a method of treating BPH which avoids any undue side effects due to acute hypotension (i.e., limited effects on blood pressure).

It is another object of the present invention to provide pharmaceutical compositions comprising 7-oxo-7H-thieno [3,2-b]pyran compounds which are selective $\alpha_1$ adrenoceptor antagonists, which compositions are effective for the treatment of BPH optionally including a carrier or diluent.

It is another object of the present invention to provide a method of treating BPH using 7-oxo-7H-thieno[3,2-b]pyran compounds which are selective $\alpha_1$ adrenoceptor antagonists.

Other aspects of the invention are the use of new compounds for lowering intraocular pressure, the treatment of cardiac arrhythmia and erectile dysfunction, treatment of sympathetically mediated pain, treatment of NLUTD, and treatment of LUTS in males and females.

In another aspect of the invention, compounds of the invention are administered in combination with anticholinergic compounds.

23 Claims, No Drawings

U.S. PATENT DOCUMENTS

| | | | |
|---|---|---|---|
| 5,091,182 | 2/1992 | Ong et al. | 424/400 |
| 5,403,842 | 4/1995 | Leonardi et al. | 514/252 |
| 5,474,994 | 12/1995 | Leonardi et al. | 514/218 |
| 5,605,896 | 2/1997 | Leonardi et al. | 514/218 |

FOREIGN PATENT DOCUMENTS

| | | | |
|---|---|---|---|
| 0 748 800 A2 | 12/1996 | (EP) | |
| 0 748 800 A3 | 12/1996 | (EP) | |
| 2 161 807 A | 1/1986 | (GB) | |
| WO 99 06382 A1 | 2/1999 | (WO) | C07D/295/10 |
| WO 99 06384 A1 | 2/1999 | (WO) | C07D/295/12 |

OTHER PUBLICATIONS

Andersson, K.E. et al., "Benign Prostatic Hyperplasia and α–Adrenoceptors in the Lower Urinary Tract"; 4th Intl. Consult. in BPH Paris, Jul. 2–5, pp. 601–609 (1997).

Andersson, K.E., "Mode of Action of $\alpha_1$_Adrenoreceptor Antagonists in the Treatment of Lower Urinary Tract Symptoms"; Brit. J. Urol. Intl. 85, Supp. 2:, pp. 12–18 (2000).

Banks, Malcolm, R., "Fries Rearrangement of Some 3–Acetoxy–and 3–Propionyloxy–Thiophenes", J. Chem. Soc. Perkin Trans, pp. 507–513 (1986).

Brougham, Paul, et al. "Oxidation Reactions Using Magnesium Monoperphthalate: A comparison With m–Chloroperoxybenzoic Acid"; "Synthesis", pp. 1015–1017 (1987).

Cheng, Yung–Chi, et al., "Relationship Between the Inhibition Constant ($K_1$) and the Concentration of Inhibitor Which Causes 50 Per Cent Inhibition ($I_{50}$) of an Enzymatic Reaction", Biochemical Pharmacology, 22: 3099–3108 (1973).

Cotecchia, Susanna, et al., "Molecular Cloning and Expression of the cDNA for the Hamster $\alpha_1$–Adrenergic Receptor", Proc. Natl. Acad. Sci. USA, 85: 7159–7163 (1988).

Cullen, Bryan R., "Use of Eukaryotic Expression Technology in the Functional Analysis of Cloned Genes", Methods in Enzymology, 152:684–704 (1987).

DeLean, A., et al.; "Simultaneous Analysis of Families of Sigmoidal Curves: Application to Bioassay, Radioligand Assay, and Physiological Dose–Response Curves"; Am. J. Physiol, 235:E97–E102 (1978).

Doherty, Annette, M., et al., "Design and Synthesis of Potent, Selective, and Orally Active Fluorine–Containing Renin Inhibitors"; J. Med. Chem., 35: 2–14 (1992).

Elworthy, T.R., et al., "N–Arylpiperazinyl–N'–Propylamino Derivatives of Heteroaryl Amides as Functional Uroselective $\alpha_1$–Adrenoceptor Antagonists"; J. Med. Chem. 40: 2674–2687 (1997).

Fargin, Annick, et al., "Effector Coupling Mechanisms of the Cloned 5–HT1A Receptor"; J. Biological Chemistry; 284: 14848–14852 (1989).

Fargin, Annick, et al., "The Genomic Clone G–21 Which Resembles a β–Adrenergic Receptor Sequence Encodes the 5–HT $_{1A}$ Receptor"; Letters Nature; 335: 358–360 (1988).

Fitzpatrick, J.M., "Facts and Future Lines of Research In Lower Urinary Tract Symptoms in Men and Women: An Overview of the Role of $\alpha_1$–Adrenoreceptor Antagonists"; Intl. Brit. J. Urol., 85: 2: 1–5 (2000).

Flavahan, N.A., et al., "$\alpha_1$_Ädrenoceptor Subclassification in Vascular Smooth Muscle", Trends Pharmacol. Sci., 7: 347–349 (1986).

Ford, Anthony, P.D.W., et al., "RS–17053 (N–[2–(2–Cyclopropylmethoxyphenoxy)ethyl]–5–Chloro–α, α–dimethyl–1H–indole–3–ethanamine hydrochloride), a Selective $\alpha_{1A}$–Adrenoceptor Antagonist, Displays Low Affinity for Functional $\alpha_1$–Adrenoceptors in Human Prostate: Implications for Adrenoceptor Classification", American Society for Pharmacology and Experimental Therapeutics, 49:209–216 (1996).

Furchgott, R.E., "The Classification of Adrenoceptors (Adrenergic Receptors). An Evaluation From the Standpoint of Receptor Theory", Handbook of Experim. Pharmacology–New Series, Chapter 9, pp. 283–335 (1972).

Gibson, M.S., "The Chemistry of the Amino Group", John Wiley & Sons, N.Y., Chapter in S. Patai (Ed.), 45 et seq., pp. 37–66 (1968).

Gozlan, H., et al., "Photoaffinity Labelling and Solubilization of the Central 5–HT $_{1A}$ Receptor Binding Site", J. Receptor Res., 7: 195–221 (1987).

Hendrickson, James. B., et al., "Triflamides: New Acylating and Triflating Reagents", Tetrahedron Letters, 46:4607–4610 (1973).

Hieble, Paul, J., et al., "International Union of Pharmacology X. Recommendation for Nomenclature of $\alpha_1$–Adrenoceptors: Consensus Update", Pharmacol. Rev., 47: 267–270 (1995).

Imagawa, Jun–Ichi, et al., "Functional Evaluation of Sympathetically Mediated Responses in In Vivo Lower Urinary Tract of Dogs", J. Pharmacol, Methods, 22:103–111 (1989).

Ishihara, Yuji, et al., "Central Cholinergic Agents. II. [1)] Synthesis and Acethlcholinesterase Inhibitory Activities of N–[ω–[N–Alkyl–N–(phenylmethyl) Amino]alkyl]–3–Arylpropenamides", Chem. Pharm. Bull, 39: 3236–3243 (1991).

Kakizaki, M., et al., "Current View and Status of the Treatment of Lower Urinary Tract Symptoms and Neurogenic Lower Urinary Tract Dysfunction", Brit. J. Urol. Intl., 85: 2: 25–30 (2000).

Kenny, B.A., et al., "Evaluation of the Pharmacological Selectivity Profile of $\alpha_1$ Adrenoceptor Antagonists at Prostatic $\alpha_1$ Adrenoceptors: Binding, Functional and In Vivo Studies", Br. J. Pharmacol, 118: 871–878 (1996).

Kobilka, B.K., et al., "An Intronless Gene Encoding a Potential Member of the Family of Receptors Coupled To Guanine Nucleotide Regulatory Proteins", Letters to Nature, 329: 75–79 (1987).

Leonardi, A., et al., "Pharmacological Characterization of the Uroselective Alpha–1 Antagonist Rec 15/2739 (SB 216469): Role of the Alpha–1L Adrenoceptor in Tissue Selectivity, Part 1", J. Pharmacol. Exp. Ther. 281:1272–1283 (1997).

Lipton, Michael, F., et al., "Conversion of Esters to Amides With Dimethylaluminum Amides: N,N–Dimethycyclohexanecarboxamide", Organic Synthesis., 59: 49–53 (1979).

Malloy, Brian J., et al., "$\alpha_1$–Adrenergic Receptor Subtypes in Human Detrusor", J. Urol., 160: 937–943 (1998).

McGrath, J.C., et al., "Alpha–Adrenoceptors: A Critical Review", Medicinal Research Reviews, 9:407–533 (1989).

McGuire, Edward, J., et al.; "Effect of Alpha–adrenergic Blockade and Anticholinergic Agents on the Decentralized Primate Bladder", Neurology and Urodinamics, 4:139–142 (1985).

Michel, Martin, C., et al., "Radioligand Binding Studies of $\alpha_1$–Adrenoceptor Subtypes in Rat Heart", Brit. J. Pharmacol, 11: 533–538 (1994).

Mitchell, James A, et al., "Preparation of Aliphatic Amides" (Chemical Abstracts), J. Am. Chem. Soc., 25: 2072–2073 (1931).

Mitchell, James A, et al., "The Preparation of Aliphatic Amides", J. Am. Chem. Soc., 53:1879–1883 (1931).

Muramatsu, Ikunobu, et al., "Functional Subclassification of Vascular $\alpha_1$–Adrenoceptors", Pharmacology Communications, 6: 23–28 (1995).

Oshita, Masafumi, et al., "Pharmacological Characterization of Two Distinct $\alpha_1$–Adrenoceptor Subtypes in Rabbit Thoracic Aorta", Br. J. Pharmacol., 108: 1071–1076 (1993).

Prelog, V., et al., Collect. Czech. Chem. Comm. 5: 497–502 (1933).

Riva, Carlo, et al., "New DBU (1,8–Diazabicyclo[5.4.O] undec–7–ene) Assisted One–Pot Synthesis of 2,8–Disubstituted 4H–1–Benzopyran–4–Ones", Synthesis, Feb. 1997, pp. 195–201 (1997).

Schwinn, Debra, A., et al., "Molecular Cloning and Expression of the cDNA for a Novel $\alpha_1$–Adrenergic Receptor Subtype", J. Biol. Chem, 265:14: 8183–8189 (1990).

Serels, Scott, et al., "Prospective Study Comparing Hyoscyamine, Doxazosin, and Combination Therapy for the Treatment of Urgency and Frequency in Women", Neurology and Urodynamics, 17: 31–36 (1998).

Sundin, Torsten., et al., "The Sympathetic Innervation and Adrenoreceptor Function of the Human Lower Urinary Tract in the Normal State and After Parasympathetic Denervation", Investigative Urology, 14:322–328 (1977).

Swierzewski, Staney, J., et al., "The Effect of Terazosin on Bladder Function in the Spinal Cord Injured Patient", J. Urology., 151: 951–954 (1994).

Testa, Rudolfo, et al., "Characterization of $\alpha_1$–Adrenoceptor Subtypes in Prostate and Prostatic Urethra of Rat, Rabbit, Dog and Man", European Journal of Pharmacology, 249: 307–315 (1993).

Testa, R., et al., "Pharmacological Characterization of the Uroselective Alpha–1 Antagonist Rec 15/2739 (SB 216469): Role of the Alpha–1L Adrenoceptor in Tissue Selectivity, Part II", J. Pharmacology and Experimental Therapeutics, 281:1284–1293 (1997).

Testa, R., et al., "Rec 15/2739 (SB 216469): A Novel Prostate Selective $\alpha_1$–Adrenoceptor Antagonist", Pharmacology Communications, 6:79–86 (1995).

Basha, Anwer, et al., "A Mild, General Method for Conversion of Esters to Amides", Tetrahedron Letters, 48: 4171–4174 (1977.-

THIENOPYRANCECARBOXAMIDE DERIVATIVES

The enclosed application is based on Provisional Patent Application Ser. No. 60/179,423 filed Jan. 31, 2000. Applicants claim the benefit of the filing date of the aforesaid Provisional Application under 35 U.S.C. §119(e)(1).

SCOPE OF THE INVENTION

The present invention relates to thienopyranecarboxamide derivatives, to pharmaceutical compositions containing them and to uses for such derivatives and compositions.

BACKGROUND OF THE INVENTION

U.S. Pat. No. 5,403,842, Leonardi et al., and its continuations in part (U.S. Pat. Nos. 5,474,994 and 5,605,896) claim heterobicyclic derivatives bearing substituted phenylpiperazines as basic moieties linked to the heterocyclic ring by a variety of spacer groups. Among said derivatives, compound A (Ex. 11) is of relevant interest due its very high uroselective activity.

Compound A

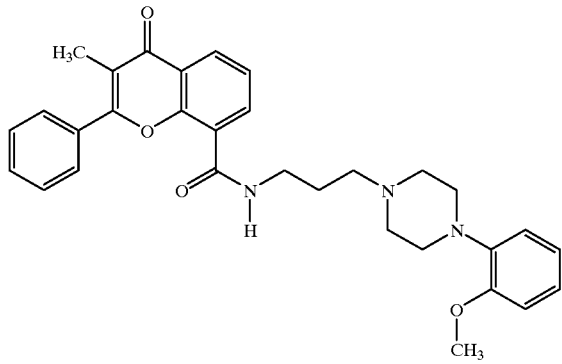

Compound A is endowed with good affinity for the $\alpha_{1A}$ adrenoceptor and is able to selectively inhibit contractility of the prostatic urethra in a dog model without substantial effects on blood pressure (Leonardi et al., J. Pharmacol. Exp. Therap., 281:1272–1283, 1997.)

7-Oxo-7H-thieno[3,2-b]pyran-3-carboxylic acid and its N,ω-aminoalkylamides are compounds not yet reported in the literature. The present invention is directed to the new structural class of the N-(substituted phenyl)-N'-[ω-(5-substituted-7-oxo-7H-thieno[3,2-b]pyran-3-carbonylamino)alkyl]piperazines.

Compounds of this class are endowed with enhanced selectivity toward the $\alpha_1$ adrenergic receptor (with or without further selectivity for the $\alpha_{1A}$ receptor or for both $\alpha_{1A}$ and $\alpha_{1D}$), in particular with respect to the 5-HT$_{1A}$ receptor, and improved in vivo uroselectivity even compared to compound A, with remarkable effects on relaxation of prostatic urethra and very low activity in lowering blood pressure. This activity profile suggests the safer use of the compounds of the invention in the therapy of obstructive syndromes of the lower urinary tract, including benign prostatic hyperplasia (BPH), and of lower urinary tract symptoms (LUTS) as well as of neurogenic lower urinary tract dysfunction (NLUTD), without side-effects associated with hypotensive activity.

SUMMARY OF THE INVENTION

In one aspect, the invention is directed to compounds of Formula I:

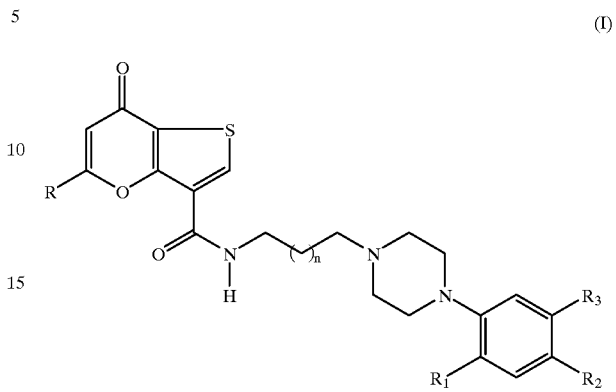

(I)

wherein
R is an aryl, cycloalkyl or polyhaloalkyl group,
$R_1$ is chosen from the group consisting of alkyl, alkoxy, polyfluoroalkoxy, hydroxy and trifluoromethanesulfonyloxy; each of $R_2$ and $R_3$ independently is chosen from the group consisting of a hydrogen, halogen, alkoxy and polyfluoroalkoxy group, and n is 0, 1 or 2.

The preferred aryl group which R may represent without limitation is phenyl. The preferred cycloalkyl group that R may represent without limitation is cyclohexyl. The preferred polyhaloalkyl group that R may represent without limitation is trifluoromethyl. The preferred alkyl group which $R_1$ may represent without limitation is $C_{1-4}$ lower alkyl. Preferred alkoxy groups ($C_{1-4}$) which $R_1$, $R_2$, and $R_3$ may represent without limitation are lower alkoxy groups, most preferably methoxy. Preferred polyfluoroalkoxy which $R_1$, $R_2$, and $R_3$ may represent without limitation are trifluoromethoxy or 2,2,2-trifluoroethoxy.

The preferred value for n is 1.

Also preferred is where $R_1$ is chosen from the group consisting of alkoxy and hydroxy; $R_2$ is chosen from the group consisting of hydrogen and halogen; $R_3$ is chosen from the group consisting of hydrogen and halogen; and n is 0, 1 or 2.

Also preferred is where $R_1$ is chosen from a group consisting of alkoxy, hydroxy and polyfluoroalkoxy; $R_2$ is chosen from the group consisting of hydrogen, halogen and alkoxy; $R_3$ is chosen from the group consisting of hydrogen, halogen and alkoxy; and n is 0, 1 or 2.

Also preferred is where $R_1$ is chosen from the group consisting of alkoxy, polyfluoroalkoxy, hydroxy; $R_2$ is halogen; $R_3$ is hydrogen; and n is 0, 1 or 2.

The invention also includes the N-oxides and pharmaceutically acceptable salts of these compounds.

The invention further provides pharmaceutical compositions comprising a compound of Formula I or a N-oxide or pharmaceutically acceptable salt of such a compound in admixture with a pharmaceutically acceptable diluent or carrier.

In another aspect, the present invention is directed to methods for selectively preventing contractions (including noradrenaline-mediated contractions) of the urethra and lower urinary tract, without substantially affecting blood pressure, by administering one or more selected compounds of Formula I to a mammal (including a human) in need of such treatment in an amount or amounts effective for the particular use.

In yet another aspect, the invention is directed to methods for blocking $a_1$ receptors, by delivering to the environment of said receptors, e.g., to the extracellular medium, (or by administering to a mammal possessing said receptors) an effective amount of a compound of the invention, in this way relieving diseases associated to overactivity of said receptors.

The very high uroselectivity of the compounds of this invention has been tested in the dog model described in Example 10, where their efficacy in antagonizing the contractions of prostatic urethra in the presence of very limited effects on blood pressure has been shown, in comparison to compound A and to another well-known $\alpha_1$-antagonist, prazosin.

Accordingly, it is a primary object of the present invention to provide a method of treating BPH which avoids any undue side effects due to acute hypotension (i.e., limited effects on blood pressure).

It is another object of the present invention to provide pharmaceutical compositions comprising 7-oxo-7H-thieno[3,2-b]pyran compounds which are selective $a_1$ adrenoceptor antagonists, which compositions are effective for the treatment of BPH optionally including a carrier or diluent.

It is another object of the present invention to provide a method of treating BPH using 7-oxo-7H-thieno[3,2-b]pyran compounds which are selective $\alpha_1$ adrenoceptor antagonists.

Another aspect of the invention is the use of new compounds for lowering intraocular pressure, inhibiting cholesterol synthesis, reducing sympathetically-mediated pain, the treatment of cardiac arrhythmia and erectile dysfunction, as well as treatment of LUTS and NLUTD.

An object of the present invention is to provide a method of preventing contractions of the urethra and lower urinary tract comprising administering to a mammal including a human in need of such treatment an effective amount of compounds of the present invention and/or pharmaceutical compositions comprising compounds of the present invention.

A further object of the present invention is a method of administration of compounds of the present invention or pharmaceutical compositions comprising compounds of the present invention to mammals including humans which causes very limited effects on the blood pressure of said mammal.

A further object of the present invention is a method for blocking $a_1$ adrenergic receptors comprising releasing in the environment of said receptors compounds of the present inventions or pharmaceutical compositions of the present invention to relieve diseases associated with overactivity of said receptor.

A further object of the present invention is the release of compounds of the present invention or pharmaceutical compositions containing compounds of the present invention in the environment of $\alpha_1$ adrenergic receptors wherein said release is effected by administering compounds of the present invention or pharmaceutical compositions containing compounds of the present invention to a mammal including a human possessing said receptors.

A further object of the present invention is the method of treatment of a patient suffering from benign prostatic hyperplasia, the method comprising administering an effective amount of a compound of the present invention or a pharmaceutical composition containing a compound of the present invention to a patient in need of such treatment.

A further object of the present invention is the method of treatment of a patient suffering from excessive intraocular pressure, the method comprising administering an effective amount of a compound of the present invention or a pharmaceutical composition containing a compound of the present invention to a patient in need of such treatment.

A further object of the present invention is the method of treatment of a patient suffering from cardiac arrhythmia, the method comprising administering an effective amount of a compound of the present invention or a pharmaceutical composition containing a compound of the present invention to a patient in need of such treatment.

A further object of the present invention is the method of treatment of a patient suffering from erectile dysfunction, the method comprising administering an effective amount of a compound of the present invention or a pharmaceutical composition containing a compound of the present invention to a patient in need of such treatment.

A further object of the present invention is the method of treatment of a patient suffering from sexual dysfunction, the method comprising administering an effective amount of a compound of the present invention or a pharmaceutical composition containing a compound of the present invention to a patient in need of such treatment.

A further object of the present invention is the method for inhibiting cholesterol synthesis, the method comprising administering an effective amount of a compound of the present invention or a pharmaceutical composition containing a compound of the present invention to a patient in need of such treatment.

A further object of the present invention is the method for reducing sympathetically mediated pain, the method comprising administering an effective amount of a compound of the present invention or a pharmaceutical composition containing a compound of the present invention to a patient in need of such treatment.

A further object of the present invention is the method for the treatment of lower urinary tract symptoms (LUTS), which include but are not limited to filling symptoms, urgency, incontinence and nocturia, as well as voiding problems such as weak stream, hesitance, intermittency, incomplete bladder emptying and abdominal straining, the method comprising administering an effective amount of a compound of the present invention or a pharmaceutical composition containing a compound of the present invention to a patient in need of such treatment, optionally further comprising the inclusion of an anticholinergic compound which may be selected from the group consisting of tolterodine, oxybutinin, darifenacin, alvameline and temiverine.

A further object of the present invention is the method for the treatment of neurogenic lower urinary tract dysfunction (NLUTD), the method comprising administering an effective amount of a compound of the present invention or a pharmaceutical composition containing a compound of the present invention to the patient, optionally further comprising the inclusion of an anticholinergic compound which may be selected from the group consisting of tolterodine, oxybutinin, darifenacin, alvameline and temiverine.

A further object of the present invention is the treatment of LUTS in females which include but are not limited to filling symptoms, urgency, incontinence, and nocturia as well as voiding problems such as weak stream, hesitance, intermittency, incomplete bladder emptying, and abdominal straining, the method comprising administering an effective amount of a compound of the present invention or a pharmaceutical composition containing a compound of the present invention to a woman in need of such treatment, optionally further comprising the inclusion of an anticholinergic compound which may be selected from the group consisting of tolterodine, oxybutinin, darifenacin, alvameline and temiverine Other features and advantages of the present invention will be apparent to those skilled in the art from the following detailed description and claims.

DETAILED DESCRIPTION OF THE INVENTION

All patents, patent applications and literature references cited in this application are incorporated by reference in their entirety.

The adrenergic antagonistic activity of the compounds of the invention renders them useful as agents acting on body tissues particularly rich in $\alpha_1$-adrenergic receptors (such as prostate and urethra). Accordingly, the anti-adrenergic compounds within the invention, established as such on the basis of their receptor binding profile, can be useful therapeutic agents for the treatment, for example, of micturition problems associated with obstructive disorders of the lower urinary tract, including but not limited to benign prostatic hypertrophy (BPH).

BPH is a progressive condition, which is characterised by a nodular enlargement of prostatic tissue resulting in obstruction of the urethra. This results in increased frequency of urination, nocturia, a poor urinary stream and hesitancy or delay in starting urine flow. Chronic consequences of BPH can include hypertrophy of bladder smooth muscle, a decompensated bladder and an increased incidence of urinary tract infection. The specific biochemical, histological and pharmacological properties of a prostate adenoma leading to the bladder outlet obstruction are not yet known. However, the development of BPH is considered to be an inescapable phenomenon for the ageing male population. BPH is observed in approximately 70% of males over the age of 70. Currently, the worldwide stated method of choice for treating BPH is surgery. A medicinal alternative to surgery is clearly very desirable. The limitations of surgery for treating BPH include the morbidity rate of an operative procedure in elderly men, persistence or recurrence of obstructive and irritative symptoms, as well as the significant cost of surgery.

α-Adrenergic receptors (McGrath et al., Med. Res. Rev., 9:407–533, 1989) are specific neuroreceptor proteins located in the peripheral and central nervous systems on tissues and organs throughout the body. These receptors are important switches for controlling many physiological functions and, thus, represent important targets for drug development. In fact, many α-adrenergic drugs have been developed over the past 40 years. Examples include clonidine, phenoxybenzamine and prazosin, terazosin, alfuzosin, doxazosin, tamsulosin (treatment of hypertension), naphazoline (nasal decongestant), and apraclonidine (treating glaucoma). α-Adrenergic drugs can be broken down into two distinct classes: agonists (clonidine and naphazoline are agonists), which mimic the receptor activation properties of the endogenous neurotransmitter noradrenaline, and antagonists (phenoxybenzamine and prazosin, terazosin, alfuzosin, doxazosin, tamsulosin are antagonists), which act to block the effects of noradenaline. Many of these drugs are effective, but also produce unwanted side effects (for example, clonidine produces dry mouth and sedation in addition to its antihypertensive effects).

The above reported agonists are selective for the $\alpha_2$ adrenergic receptor whereas most antagonists are selective for the $\alpha_1$ adrenoceptor, with the exception of tamsulosin which shows a relevant affinity also for the 5-$HT_{1A}$ receptor.

Many of the cited $\alpha_1$ antagonists are currently used for the therapy of BPH but, due to their poor uroselectivity, they are liable to cause side effects of cardiovascular type.

Recent pharmacological, biochemical and radioligand-binding studies evidenced three different $\alpha_1$-receptor subtypes with a high affinity for prazosin, namely $\alpha_{1A\text{-}}(\alpha_{1a\text{-}})$, $\alpha_{1B\text{-}}(\alpha_{1b\text{-}})$ and $\alpha_{1D\text{-}}(\alpha_{1d\text{-}})$, with lower case subscripts being used for recombinant receptors and upper case subscripts for receptors in native tissues (Hieble et al., Pharmacol. Rev., 47:267–270, 1995). In functional studies $\alpha_1$-receptors with a low affinity for prazosin have also been identified and termed $\alpha_{1L}$-receptors (Flavahan and Vanhoutte, Trends Pharmacol. Sci., 7:347–349, 1986; Muramatsu et al., Pharmacol. Comm., 6:23–28, 1995).

Several studies have demonstrated the presence of these $\alpha_1$-adrenergic receptor subtypes in the lower-urinary-tract tissues as reviewed by (Andersson, K. E., "4th International Consultation in Benign Prostatic Hyperplasia (BPH)", Paris, Jul. 2–5, 1997, pages 601–609).

Several studies have shown that the human prostate receives innervation from both the sympathetic and parasympathetic nervous systems.

The adrenergic nerves are considered responsible for prostatic smooth-muscle tone by releasing noradrenaline, stimulating contraction-mediating α-adrenoceptors. Approximately 50% of the total urethral pressure in BPH patients may be due to α-adrenoceptor-mediated muscle tone. Functional studies have indicated the occurrence of important adrenoceptor functions in prostatic adenomatous and capsular tissue. Clinical studies with the prototypical adrenoceptor-selective antagonist, prazosin, reinforced the key role of $\alpha_1$ adrenoceptors in the control of prostatic smooth-muscle tone. This was also confirmed in the laboratory by studies showing that, although both $\alpha_{1\text{-}}$ and $\alpha_2$-adrenoceptors can be identified within the human prostate, contractile properties are mediated primarily by $\alpha_1$ adrenoceptors. Many clinical investigations have confirmed that $\alpha_1$-adrenoceptor blockade relieves lower urinary tract symptoms (LUTS), both of irritative and obstructive type, in patients with BPH.

Lower urinary tract symptoms (LUTS) also develop in women as they age. As in men, LUTS in women includes both filling symptoms such as urgency, incontinence, and nocturia, and voiding symptoms, such as weak stream, hesitancy, intermittency, incomplete bladder emptying and abdominal straining. That both men and women experience a similar high prevalence of filling and voiding LUTS suggests that at least part of the underlying etiology may be identical. In a recent study, an $\alpha_1$-antagonist was reported to reduce LUTS in women to a greater extent than an anticholinergic (Serels, S. and Stein, M., *Neurology and Urodynamics* 17: 31–36, 1998). The authors concluded that there appeared to be a role for $\alpha_1$-antagonists in treating LUTS in women. The possible mechanisms implicated to explain these results are: a) dysfunction of the bladder neck and urethra, causing functional outlet obstruction, analogous to BPH-induced outlet obstruction, with secondary detrusor overactivity; and b) increased $\alpha_1$-adrenoreceptor activity in the detrusor, causing frequency and urgency. On these bases, $\alpha_1$-antagonists are used in clinical practice to treat LUTS in women. (Fitzpatrick, *International British J. Urol.* 85, Supp. 2: 1–5 (2000); Kakizaki, M. et al., *Brit. J. Urol International* 85, Supp. 2: 25–30 (2000)). The results of Serels also indicate that the combined administration of $\alpha_1$-antagonists and anticholinergics can have improved efficacy in treatment of LUTS, as suggested by Fitzpatrick (*International British*

J. Urol. 85, Supp. 2: 1–5 (2000)). The results of Serels also indicate that the combined administration of $\alpha_1$-antagonists and anticholinergics can have improved efficacy in treatment of LUTS, as suggested by Fitzpatrick, *International British J. Urol.* 85, Supp. 2: 1–5, 2000).

Another possible use of $\alpha_1$-antagonists is the management of neurogenic lower urinary tract dysfunction (NLUTD), as can be caused by neurological disease or trauma. NLUTD may lead to debilitating symptoms and serious complications, including increased urinary frequency, incontinence, voiding difficulty, recurrent upper urinary tract infections, and upper urinary tract deterioration. Management of NLUTD is indicated to preserve renal function and avoid urological complications. Administration of $\alpha_1$-antagonists may benefit patients with NLUTD by facilitating urine storage by alleviating high detrusor pressure during bladder filling, which is evidenced by poor bladder compliance and detrusor hyperreflexia. In both animal models and patients with spinal cord injury resistant to anticholinergics, $\alpha_1$-antagonists improved bladder compliance. (Kakizaki, M. et al., *Brit. J. Urol International* 85, Supp. 2: 25–30, 2000; Sundin, T. et al., *Invest. Urol.* 14: 322–328, 1977; McGuire et al., *Neurology and Urodynamics* 4: 139–142 ,1985; Swrerzewski, S. J. et al., *J. Urol.* 151: 951–954, 1994).

Two distinct $\alpha_1$ adrenoceptor subtypes have been suggested to be present in the human prostate, one with high ($\alpha_{1H}$) and one with low ($\alpha_{1L}$) affinity for prazosin. All three high-affinity $\alpha_1$ adrenoceptor subtypes found in molecular cloning studies have been identified in prostatic stromal tissue. The $\alpha_{1a}$ subtype was found to be the dominant, representing about 60–85% of the $\alpha_1$ adrenoceptor population. Recent findings suggest that there may be differences in subtype populations between normal and hyperplastic prostates, the ratios between the subtypes $\alpha_{1a}:\alpha_{1b}:\alpha_{1d}$ being 85:1:14 in BPH and 63:6:31 in non-BPH tissue.

The $\alpha_{1A}$ adrenoceptor was reported to mediate the contractile response of the human prostate in vitro. Ford et al. found that the $\alpha_{1A}$ adrenoceptor may not mediate contractile responses to noradrenaline, and suggested as a candidate the $\alpha_{1L}$ adrenoceptor. Findings by Kenny et al. (Br. J. Pharmacol., 118:871–878, 1996) support the view that the $\alpha_{1L}$ adrenoceptor, which appears to share many of the characteristics of an $\alpha_{1A}$ adrenoceptor, mediates the contractile response of the human prostate.

On the other hand, it has also been suggested that the $\alpha_{1A}$ and $\alpha_{1L}$ adrenoceptors may represent distinct pharmacological forms of the same receptor.

In the female urethra, mRNA for the $\alpha_1$ subtype was predominant and autoradiography confirmed the predominance of the $\alpha_{1A}$ adrenoceptor (Andersson, K. E., *Brit. J. Urol. Intl.* 85, Supp. 2: 12–18, 2000). The $\alpha_{1A}$ and $\alpha_{1D}$ subtypes are reported to be present in the human detrusor, with the latter subtype predominant (Malloy, B. et al., *J. Urol* 160: 937–943, 1998). Accordingly, the evidence that $\alpha_1$ adrenoreceptor antagonists are useful in treating lower urinary tract symptoms of both prostatic and non-prostatic origin in both males and females can be used to support the usefulness of the compounds of the present invention in treating such symptoms regardless of whether they are of obstructive origin or not and regardless of the sex of the patient.

The affinity of the compounds of the invention for each receptor can be assessed by receptor binding assays, for example as follows:

(1) $\alpha_1$-adrenergic-receptor subtypes: using the specific ligand $^3$H-prazosin, according to Testa et al., *Pharmacol.* *Comm.* 6: 79–86, 1995; Cotecchia, S., Schwinn, D. A., Randall, R. R. and Lefkowitz, F. J., *Proc. Natl. Acad. Sci. USA*, 85: 7159–7163 (1988); Furchgott. R. E., *Handbook of Experimental Pharmacology—New Series*, 283–335 (1972); Michel, M. C., Hanft, G. and Gross, G., *Brit. J. Pharmacol.* 111: 533–538 (1994); Schwinn, D. A., Lomasney, J. W., Lorenz, W., Szklut, P. J., Fremcau, R. T., Yang-Feng, T. L., Caron, M. G., Lefkowitz, R. J. and Cotecchia, S., *J. Biol. Chem.* 265: 8183–8189 (1990); Testa, R., Guarneri, L., Ibba, M., Strada, G., Poggesi, E., Taddei, C., Simonazzi, I. and Leonardi, A. *Europ. J. Pharmacol.* 249: 307–315 (1993).

(2) $5HT_{1A}$-serotonergic receptor: using the specific ligand $^3$H-8-OH-DPAT according to Fargin et al., *Nature* 335: 358–360, (1988); Kobilka, B. K. et al., *Nature* 329: 75–79 (1987); Cullen, B. R., *Meth. Enzym.* 152: 684–704 (1987); Gozlan, H. et al., *J. Receptor Res.* 7: 195–221 (1987).

The $\alpha_{1L}$-adrenergic receptor is not yet cloned and, therefore, the functional affinity of the compounds of the invention for this subtype can be assessed by using an isolated organ preparation as reported by Testa et al., *J. Pharmacol. Exp. Ther.* 281: 1284–1293, (1997); Oshita, M., Kigoshi, S. and Muramatsu, I., *Br. J. Pharmacol.* 108: 1071–1076 (1993).

In vitro testing of the compounds of this invention on the above receptors is described in Examples 8 and 9 below.

The drugs having $\alpha_1$-adrenergic antagonistic activity currently used for the symptomatic therapy of BPH are poorly subtype selective and subject to cause relevant side effects due to their hypotensive activity.

Thus there is a need for selective $\alpha_1$-antagonists which do not subject the BPH patient to the side effects, especially the cardiovascular side effects of said treatment.

The high uroselectivity of the compounds of the invention has been demonstrated by the dog model of the Example 10 below, where their efficacy in counteracting the contractions of prostatic urethra at doses that do not influence blood pressure has been shown.

SYNTHESIS OF THE COMPOUNDS OF THE INVENTION

The compounds according to the invention may be generally prepared as follows:

Direct condensation of 7-oxo-7H-thieno[3,2-b]pyran-3-carboxylic acids of the formula I with the ω-aminoalkylamino derivatives 2 (SCHEME 1) leads to the compounds of the invention. The condensation can be carried out in the presence of a condensing agent (e.g., dicyclohexylcarbodiimide or diethyl cyanophosphonate) optionally in the presence of a promoting agent (e.g., N-hydroxysuccinimide, 4-dimethylaminopyridine or N,N'-carbonyldiimidazole) in an aprotic or chlorinated solvent (e.g., N,N-dimethylformamide or chloroform) at −10/140° C. (Albertson, Org. React., 12:205–218, 1962; Doherty et al., J. Med. Chem., 35:2–14, 1992; Ishihara, Chem. Pharm. Bull., 39:3236–3243, 1991). In some cases the activated ester or amide intermediates (such as O-(N-succinimidyl) esters or acyl imidazolides) can be isolated and further reacted with 2 to be transformed into the corresponding amides (I) in an aprotic or chlorinated solvent at 10/100° C. This kind of condensation is well illustrated in the Scheme 1

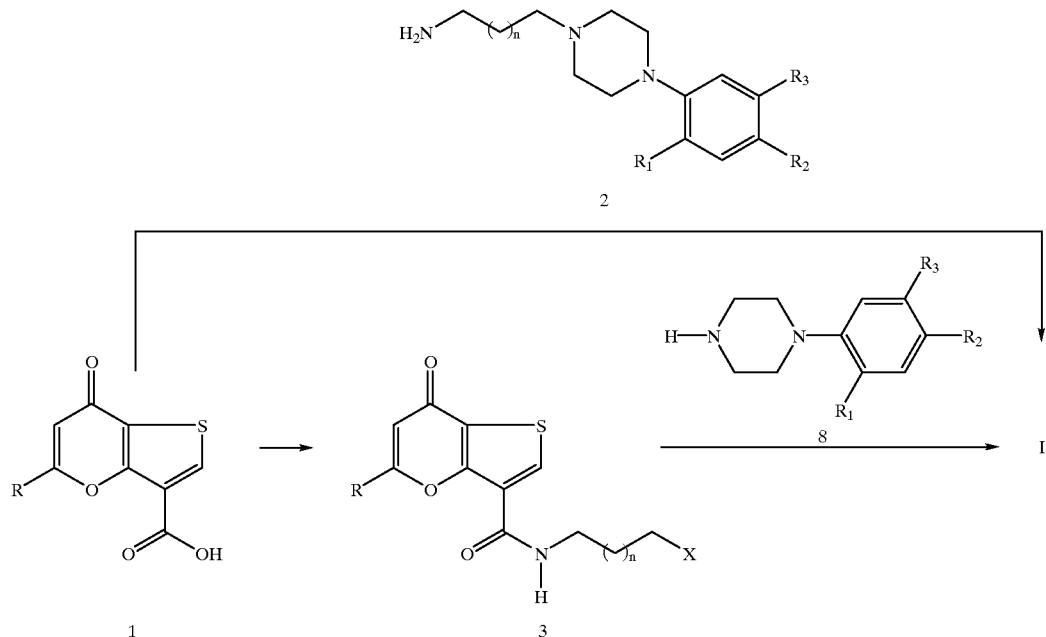

Examples. Another activated intermediate which can be used is the mixed anhydride of 1, obtainable reacting 1 with an alkyl chloroformate in the presence of a tertiary amine (e.g., triethylamine or N-methylmorpholine), which is reacted with 2 at 0–80° C.; optionally a promoting agent (e.g., 1-hydroxypiperidine) may be added before the amine addition (Albertson, Org. React., 12:157, 1962).

Alternatively the condensation can be carried out without a solvent at 150–220° C. (Mitchell et al., J. Am. Chem. Soc., 53; 1879, 1931) or in high-boiling ethereal solvents (e.g., diglyme).

The condensation can also be performed through preparation and optional isolation of reactive derivatives of 1 such as acyl halides. Formation of acyl halides of compounds of formula 1 and reactions with amines 2 to form amides is well documented in the literature and known to people skilled in the art.

Also less reactive derivatives of 1 can be used, such as alkyl esters, which in turn can be converted into I in the presence of a condensing agent (e.g., trimethylaluminum) in an aprotic and/or chlorinated solvent (e.g., hexane, dichloromethane) at −10/80° C., or without solvents at 80–180° C., (Weinreb et al., Tetrahedron Lett., 4171, 1977; Lipton et al., Org. Synth., 59:49, 1979).

By the same methods of condensation reported above and using $H_2NCH_2(CH_2)_nCH_2X$ (with X=halogen or OH) as a reagent, 1 can be transformed into 3. In the case of X=OH, the alcoholic group is then converted into a suitable leaving group by methods well known to those skilled in the art. Compounds 3 (with X=leaving group such as halogen or alky/arylsulphonyloxy group) can be subsequently reacted with an appropriate phenylpiperazine 8 bearing the desired phenyl group. The nucleophilic substitution is carried out preferably, but not necessarily, at a temperature within the range of 20–200° C. in a polar solvent such as dimethylformamide, acetonitrile, methanol, or without any solvent, usually in the presence of a base such as potassium carbonate. See also Gibson's chapter in Patai: "The Chemistry of the Amino Group", p. 45 et seq., Wiley International Science, N.Y., 1968.

The preparation of compounds 2 which are not commercially available is disclosed in the literature and is well known to those skilled in the art, and is usually carried out performing nucleophilic substitution of a phenylpiperazine 8 on a N-(ω-haloalkyl)phthalimide or a proper ω-haloalkylnitrile or haloalkylamide by the method illustrated above for the condensation of compounds 3 and 8, or by addition of an α,β-unsaturated alkylnitrile or alkylamide in a proper solvent (e.g., acetonitrile, dimethylformamide, a chlorinated solvent or other aprotic polar solvent) at a temperature between 0° C. and the reflux temperature of the solvent. Standard phthalimido-group deprotection or reduction of the amido or cyano group then provides compounds 2, and can be performed by methods well known to those skilled in the art.

The acids 1 of the invention in which R represents cycloalkyl or aryl group can be synthesized (SCHEME 2) starting from methyl 2-acetyl-3-hydroxythiophene-4-carboxylate (prepared as described in J. Chem. Soc. Perkin Trans I, 507, 1986), which can be esterified with the proper alkanoyl or aroyl chloride by using methods very well known to those skilled in the art. Alternative procedures include the same methods described above for the amidification of 1, which could be applied as well in the esterification step to afford 4.

Scheme 2

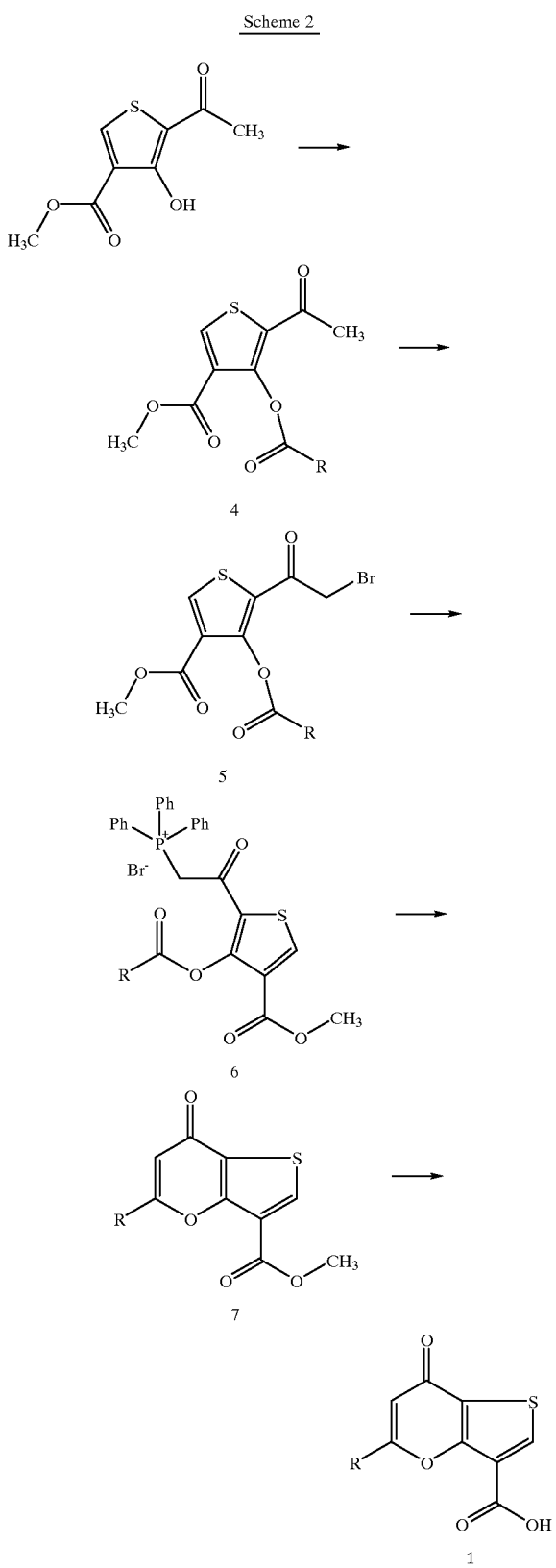

Monobromination of the methylketo group of 4 can afford 5, which can then be reacted with triphenylphosphine (typically by reflux in acetonitrile, toluene, or other aprotic solvent), to give the phosphonium salt 6. A subsequent intramolecular ester-Wittig reaction applied to this substrate yields the thieno[3,2-b]pyranes, 7. Hydrolysis of the ester group of compounds 7 is accomplished by acid or base catalysed procedures that are well known to those skilled in the art, yielding compounds 1.

Such hydrolysis procedures include the use of sodium hydroxide in aqueous ethanol at 40–75° C., or lithium hydroxide in aqueous dimethylformamide, or tetrahydrofuran at 40–100° C.

The compounds 1 where R is a polyfluoroalkyl group can be prepared from 2-acetyl-3-hydroxythiophene-4-carboxylate following the cyclization procedure described by Riva et al., (Synthesis, 195–201, 1997) by direct cyclization in the presence of anhydrous polyfluoroalkanoyl anhydrides catalysed by 1,8-diazabicycloundec-7-ene.

The compounds I where $R_1$ is a trifluoromethanesulphonyloxy group can be synthesized starting from compounds I where $R_1$ is a hydroxy group using procedures well known to those skilled in the art, by way of example without limitation, using trifluoromethanesulphonic anhydride or N-phenyltrifluoromethanesulphonimide in aprotic solvents such as 1,2-dichloroethane or other chlorinated solvents or toluene, at a temperature in the range between 20° C. and the temperature of reflux of the solvent (Hendickson et al., Tetrahedron Letters, 4607–4510, 1973). The N-oxides of the compounds I may be synthesized by simple oxidation procedures known to those skilled in the art. The oxidation procedure described in P. Brougham in Synthesis, 1015–1017 (1987) allows differentiation of the two nitrogen atoms of the piperazine ring and both the N-oxides and N,N'-dioxides to be obtained.

Preparation of the phenylpiperazines 8, which has not been described in the literature, is well documented in the examples and uses synthetic procedures well known to those skilled in the art, which comprise the synthesis of the proper aniline through standard reactions and the subsequent cyclization with bis-(2-chloroethyl)amine to afford the piperazine following the method of Prelog (Collect. Czech.Chem.Comm., 5:497–502, 1933) or its variations (Elworthy, J. Med. Chem., 40:2674–2687, 1997).

DETAILED SYNTHESIS OF THE COMPOUNDS OF THE INVENTION

Below are some examples intended only to illustrate the invention so as described in the test, with no intention to limit it.

EXAMPLE 1

N-{3-[4-(5-Chloro-2-methoxyphenyl)-1-piperazinyl] propyl}-7-oxo-5-phenyl-7H-thieno [3,2-b]pyran-3-carboxamide a) 1-(5-Chloro-2-methoxyphenyl)-4-[3-(N-phthalimido) propyl]piperazine (Compound 1A)

A mixture of of 28.64 g of 1-(5-chloro-2-methoxyphenyl) piperazine, 44.6 g of anhydrous potassium carbonate and 33.65 g of N-(3-bromopropyl)phthalimide in 250 mL of acetonitrile was stirred at reflux for 8 hours. After cooling to 20–25° C., 800 mL of water was added under stirring and the resulting suspension was filtered by suction yielding a yellowish solid, which was washed with 300 mL of water and crystallised from methanol affording 46.5 g of the title compound, melting at 131–133° C.

| $^1$H-NMR (200 MHz) spectrum | | | Solvent CDCl$_3$, Chemical shift ($\delta$) |
|---|---|---|---|
| 7.78–7.82 | m | 2 H | phthalimide H3, H6 |
| 7.64–7.78 | m | 2 H | phthalimide H4, H5 |
| 6.92 | dd | 1 H | methoxyphenyl H4 |
| 6.65–6.78 | m | 2 H | methoxyphenyl H3, H6 |
| 3.81 | s | 3 H | CH$_3$O |
| 3.71–3.89 | m | 2 H | CH$_2$N(CO)$_2$ |
| 2.78–3.00 | m | 4 H | 3 and 5 piperazine CH$_2$s |
| 2.40–2.65 | m | 6 H | 2 and 6 piperazine CH$_2$s, CH$_2$CH$_2$CH$_2$N(CO)$_2$ |
| 1.80–2.03 | m | 2 H | CH$_2$CH$_2$CH$_2$ | b) 1-(3-Aminopropyl)-4-(5-chloro-2-methoxyphenyl) piperazine trihydrochloride.2.15 H$_2$O (Compound 1B)

A solution of 20.7 g of Compound 1A and 8.6 mL of 85% hydrazine hydrate in 300 mL of ethanol were stirred at reflux for 3.5 hours. Afterwards, the reaction mixture was cooled to 20–25° C., diluted with 400 mL of water, acidified with 37% hydrochloric acid (pH=1and stirred for 0.5 hour. The precipitated solid was collected by filtration and washed with 1N hydrochloric acid followed by water. The filtrate was concentrated by evaporation in vacuo, filtered, made basic by addition of 35% sodium hydroxide at 0–5° C. and extracted with diethyl ether. The organic layer was washed with brine, dried on sodium sulphate and evaporated to dryness in vacuo affording 13.6 g (96%) of the title compound as a base. Acidification of the solution of the base in chloroform with more than three equivalents of 3N ethanolic hydrogen chloride followed by evaporation to dryness in vacuo and crystallization of the residue from ethanol/diethyl-ether 10:3 yielded the title compound, melting at 200–202° C.

| $^1$H-NMR (200 MHz) spectrum | | | Solvent DMSOd$_6$, Chemical shift ($\delta$) |
|---|---|---|---|
| 11.20–11.50 | br | 1 H | NH$^+$ |
| 8.10–8.40 | br | 3 H | NH3$^+$ |
| 6.85–7.10 | m | 3 H | phenyl H3, H4, and H6 |
| 5.10 | br | 5.3 H | NH$^+$, 2.15 H$_2$O |
| 3.79 | s | 3 H | CH$_3$O |
| 3.35–3.65 | m | 4 H | 2 piperazine CH2s |
| 3.03–3.35 | m | 6 H | 2 piperazine CH2s, CH$_2$CH$_2$CH$_2$NH$_3^-$ |
| 2.80–3.03 | m | 2 H | CH$_2$CH$_2$CH$_2$NH$_3^+$ |
| 1.95–2.22 | m | 2 H | CH$_2$CH$_2$CH$_2$NH$_3^+$ | c) Methyl 2-acetyl-3-benzoyloxythiophene-4-carboxylate (Compound 1C)

3.48 mL of benzoyl chloride was added dropwise to a solution of 5.0 g of methyl 2-acetyl-3-hydroxythiophene-4-carboxylate (prepared as described in J. Chem. Soc. Perkin Trans I, 1986, 507) and 3.66 g of 4-dimethylaminopyridine in 100 mL of dichloromethane at 20–25° C. and stirred for 2 hours. The mixture was washed with 0.5N hydrochloric acid, water (2×20 mL), 2.5% aqueous sodium bicarbonate (2×40 mL) and water (2×20 mL). The organic layer was dried with sodium sulphate, evaporated to dryness in vacuo and purified by flash chromatography using chloroform/ethyl-acetate (100:1). The yield of Compound 1C was 7.089, as a yellow deliquescent solid, which was used in the next step without further purification.

| $^1$H-NMR (200 MHz) spectrum | | | Solvent CDCl$_3$, Chemical shift ($\delta$) |
|---|---|---|---|
| 8.36 | s | 1 H | thiophene H5 |
| 8.20–8.42 | m | 2 H | phenyl H2, H6 |
| 7.52–7.78 | m | 3 H | phenyl H3, H4, H5 |
| 3.73 | s | 3 H | CH$_3$O |
| 2.50 | s | 3 H | CH$_3$CO | d) Methyl 2-(2-bromoacetyl)-3-benzoyloxythiophene-4-carboxylate (Compound 1D)

A solution of 1.28 mL of bromine in 24 mL of tetrachloromethane was added dropwise to a solution of 7.23 g of Compound 1C in 72 mL of tetrachloromethane over a period of 10 minutes and stirred at reflux. After a further 5 minutes at reflux, the mixture was cooled to 20–25° C. The precipitated solid was collected by filtration and washed with cold tetrachloromethane to yield 7 g (77%) of Compound 1D, melting at 115–118° C. The compound was contaminated with impurities 1B and methyl 2-(2,2-dibromoacetyl)-3-benzoyloxythiophene-4-carboxylate (2% and 6% mol. respectively, determined by $^1$H-NMR spectroscopy), but could be used without further purification in the next reaction step.

| $^1$H-NMR (200 MHz) spectrum | | | Solvent CDCl$_3$, Chemical shift ($\delta$) |
|---|---|---|---|
| 8.43 | s | 1 H | thiophene H5 |
| 8.20–8.42 | m | 2 H | phenyl H2, H6 |
| 7.52–7.80 | m | 3 H | phenyl H3, H4, H5 |
| 6.70 | s | 0.06 H | CHBr$_2$ |
| 4.30 | s | 1.84 H | CH$_2$Br |
| 3.73 | s | 3 H | CH$_3$O |
| 2.50 | s | 0.06 H | CH$_3$CO | e) 2-[(3-Benzoyloxy-4-methoxycarbonl)-2-thienyl]-2-oxoethyltriphenylphosphonium bromide hemihydrate (Compound 1E)

A solution of 6.9 g of compound 1D and 5.19 g of triphenylphosphine in 45 mL of acetonitrile was stirred at reflux for 4 hours and then cooled to 20–25° C. The precipitate was collected by filtration to yield 10.27 g (88%) of Compound 1E, melting at 150–152° C., which was pure enough to be used in further reactions. 0.27 g of crude product was crystallized from i-PrOH to yield 0.24 g of the analytical sample. M.p. (124)128–132° C.

| $^1$H-NMR (200 MHz) spectrum | | | Solvent CDCl$_3$, Chemical shift ($\delta$) |
|---|---|---|---|
| 8.38–8.50 | m | 3 H | PhCO H2, H6 and thienyl H5 |
| 7.41–7.87 | m | 18 h | (C$_6$H$_5$)3P and PhCO H3, H4, H5 |
| 6.35 | d | 2 H | CH$_2$P |
| 3.71 | s | 3 H | CH$_3$O | f) Methyl 7-oxo-5-phenyl-7H-thieno[3,2-b]pyran-3-carboxylate (Compound 1F)

150 mL of 1M aqueous sodium carbonate was added to a solution of 10.07 g of Compound 1E in 200 mL of 1,2-dichloroethane and the mixture was stirred at 85° C. for 11 hours, then cooled. The organic layer was separated, washed with water to neutrality, dried over anhydrous sodium sulphate and evaporated to dryness in vacuo to yield 8.67 g of a crude residue. The crude residue was purified by flash chromatography with petroleum ether/ethyl acetate 6:4 to yield 4.1 g (92%) of Compound 1F, melting at 169–171° C.

Compound 1F was crystallized from methanol to give the analytical sample. M.p. 169–171° C.

| | | | |
|---|---|---|---|
| 8.50 | s | 1 H | H2 |
| 7.95–8.05 | m | 2 H | phenyl H2, 6 |
| 7.50–7.60 | m | 3 H | phenyl H3, 4, 5 |
| 6.88 | s | 1 H | H6 |
| 4.00 | s | 3 H | CH$_3$O | g) 7-Oxo-5-phenyl-7H-thieno[3,2-b]pyran-3-carboxylic acid (Compound 1G)

26 mL of 0.6N sodium hydroxide was added to a solution of 3.82 g of Compound 1F in 174 mL of methanol and 87 mL of dioxane at 50° C. while stirring. The mixture was stirred at 50° C. for an additional 20 minutes, cooled to 20–25° C., then diluted with 280 mL of water, filtered and acidified with 1N hydrochloric acid to pH=1. The suspension of that formed precipitate gel was stirred at 60° C. for 2 hours, until a heavier filtrable solid was obtained. This solid was filtered and dried to yield 3.4 g of the title compound, which was suitable for use in the next reaction step without further purification. It was crystallized from ethanol to yield the analytical sample, melting at 282–283° C.

| $^1$H-NMR (200 MHz) spectrum | | Solvent CDCl$_3$, Chemical shift (δ) | |
|---|---|---|---|
| 13.39 | bs | 1 H | COOH |
| 8.50 | s | 1 H | H2 |
| 8.00–8.05 | m | 2 H | phenyl H2, H6 |
| 7.52–7.60 | m | 3 H | phenyl H3, H4, H5 |
| 7.13 | s | 1 H | H6 | h) N-{3-[4-(5-Chloro-2-methoxyphenyl)-1-piperazinyl}-propyl]-7-oxo-5-phenyl-7H-thieno[3,2-b]pyran-3-carboxamide 0.54 mL of 93% diethyl cyanophosphonate and 0.46 mL of triethylamine were added to a solution of 0.82 g of Compound 1G and 0.94 g of Compound 1B base in 15 mL of anhydrous N,N-dimethylformamide at 0° C. while stirring. The mixture was stirred for 22 hours at 20–25° C., poured into 150 mL of water. The solution was decanted and the pasty precipitate that remained was dissolved in 60 mL of chloroform, washed with water, dried over sodium sulphate, and evaporated to dryness in vacuo.

The crude materials was purified by flash chromatography with ethyl acetate/methanol (9:1) and evaporated to yield the pure title compound (1.2 g; 74%), which was crystallized from EtOAc. M.p. 165–166.5° C.

| $^1$H-NMR (200 MHz) spectrum | | Solvent CDCl$_3$, Chemical shift (δ) | |
|---|---|---|---|
| 8.45 | s | 1 H | H2 |
| 7.90–8.02 | m | 2 H | phenyl H2, H6 |
| 7.55–7.62 | m | 3 H | phenyl H3, H4, H5 |
| 7.45 | t | 1 H | CONH |
| 6.95 | dd | 1 H | chlorophenyl H4 |
| 6.83 | s | 1 H | H6 |
| 6.65–6.75 | m | 2 H | chlorophenyl H3, H6 |
| 3.81 | s | 3 H | CH$_3$O |
| 3.66 | dt | 2 H | CONHCH$_2$ |
| 2.74–2.92 | m | 4 H | 2 piperazine CH$_2$s |
| 2.48–2.54 | m | 6 H | CH$_2$N and 2 piperazine CH$_2$s |
| 1.80–2.00 | m | 2 H | CH$_2$CH$_2$CH$_2$ |

EXAMPLE 2

N-{3-[4-(2-Methoxyphenyl)-1-piperazinyl]propyl}-7-oxo-5-phenyl-7H-thieno[3,2-b]pyran-3-carboxamide The title compound was prepared as described in Example 1h, but substituting 1-(3-aminopropyl)-4-(2-methoxyphenyl)piperazine (prepared as described in patent GB 2,161,807) for Compound 1B. After pouring the reaction mixture into water and extracting with ethyl acetate, the combined organic layers were washed with water (3×80 mL), dried over sodium sulphate and evaporated to dryness in vacuo. The crude product was purified by flash chromatography with ethyl acetate/methanol (8.5:1.5) and evaporated to dryness. The residue yielded the pure title compound (1.4 g; 77%), which was crystallized from EtOAc to yield the title compound melting at 161–162° C.

| $^1$H-NMR (200 MHz) spectrum | | Solvent CDCl$_3$, Chemical shift (δ) | |
|---|---|---|---|
| 8.41 | s | 1 H | H2 |
| 7.90–8.02 | m | 2 H | phenyl H2, H6 |
| 7.50–7.65 | m | 4 H | NHCO and phenyl H3, H4, H5 |
| 6.80 | s | 1 H | H6 |
| 6.70–7.05 | m | 4 H | Chs of methoxyphenyl ring |
| 3.83 | s | 3 H | CH$_3$O |
| 3.66 | dt | 2 H | CONHCH$_2$ |
| 2.80–3.00 | m | 4 H | 2 piperazine CH$_2$s |
| 2.48–2.62 | m | 6 H | CH$_2$N adn 2 piperazine CH$_2$s |
| 1.80–2.00 | m | 2 H | CH2CH$_2$CH$_2$ |

EXAMPLE 3

5-Cyclohexyl-N-{3-[4-(2-methoxyphenyl)-1-piperazinyl]propyl}-7-oxo-7H-thieno[3,2-b]pyran-3-carboxamide a) Methyl 2-acetyl-3-cyclohexanecarbonyloxythiophene-4-carboxylate (Compound 3A)

This compound was prepared as described for compound 1C of Example 1, but using cyclohexanecarbonyl chloride instead of benzoyl chloride. The crude product was purified by flash chromatography using a petroleum ether/ethyl acetate gradient from 9:1 to 7:3 to afford Compound 3A (80%).

| $^1$H-NMR (200 MHz) spectrum | | Solvent CDCl$_3$, Chemical shift (δ) | |
|---|---|---|---|
| 8.30 | s | 1 H | thiophene H5 |
| 3.80 | s | 3 H | CH$_3$O |
| 2.50 | s | 3 H | CH$_3$CO |
| 1.00–3.00 | m | 11 H | cyclohexane CHs | b) Methyl 2-(2-bromoacetyl)-3-cyclohexanecarbonyloxythiophene-4-carboxylate (Compound 3B)

A solution of 0.70 mL of bromine in 3.45 mL of acetic acid was added dropwise over a period of 60 minutes to a solution of 3.56 g of Compound 3A in 34.5 mL of acetic acid at 20–25° C. while stirring. After stirring further for 2.5 hours at 20–25° C., the mixture was poured into ice water and extracted with diethyl ether (2×80 mL). The combined organic layers were washed with water (2×80 mL), 10% aqueous sodium carbonate (100 mL) and water (3×80 mL), dried over sodium sulphate and evaporated to dryness in vacuo. The crude product was purified by flash chromatography in n-hexane/chloroform (6:4) to yield 1.31 g (29%) of Compound 3B.

| ¹H-NMR (200 MHz) spectrum | | | Solvent CDCl₃, Chemical shift (δ) |
|---|---|---|---|
| 8.36 | s | 1 H | thiophene H5 |
| 4.29 | s | 2 H | CH₂Br |
| 3.83 | s | 3 H | CH₃O |
| 2.65–2.80 | m | 1 H | cyclohexane CH |
| 2.15–2.25 | m | 2 H | 2, 6 cyclohexane CHs (eq.) |
| 1.85–1.95 | m | 2 H | 2, 6 cyclohexane CHs (ax.) |
| 1.25–1.80 | m | 6 H | 3, 4, 5 cyclohexane CH₂s | c) 2-[(3-Cyclohexanecarbonyloxy-4-methoxycarbonyl)-2-thienyl]-2-oxoethyltriphenylphosphonium bromide (Compound 3C)

A solution of 0.20 g of compound 3B and 0.13 g of triphenylphosphine in 1.25 mL of acetonitrile was stirred at reflux for 2.5 hours and then cooled to 0–5° C. The precipitate was collected by filtration, then washed on the filter with a 2:1 mixture of ethyl-acetate/acetonitrile, followed by ethyl acetate, to yield 0.19 g (59%) of Compound 3C melting at 165–167° C.

| ¹H-NMR (200 MNz) spectrum | | | Solvent CDCl₃, Chemical shift (δ) |
|---|---|---|---|
| 8.31 | s | 1 H | thiophene H5 |
| 7.55–8.00 | m | 15 H | (C₆H₅)₃ P |
| 6.35 | d | 2 H | CH₂P |
| 3.79 | s | 3 H | CH₃O |
| 2.60–2.75 | m | 1 H | cyclohexane CH |
| 1.95–2.05 | m | 2 H | 2, 6 cyclohexane CHs (eq.) |
| 1.10–1.70 | m | 8 H | other cyclohexane CHs | d) Methyl 5-cyclohexyl-7-oxo-7H-thieno[3,2-b]pyran-3-carboxylate (Compound 3D)

A mixture of 0.16 g of Compound 3C, 2 mL of 1,2-dichloroethane and 2 mL of 1M aqueous sodium carbonate was heated at 45° C. for 36 hours. After cooling to 20–25° C., 5 mL of chloroform was added, the organic layer was washed with water (2×10 mL), dried on anhydrous sodium sulphate and evaporated to dryness in vacuo. The crude product was purified by flash chromatography (petroleum ether/ethyl acetate 1:1) yielding 0.05 g (68%) of Compound 3D as a white solid, melting at 114–119° C.

| ¹H-NMR (200 MHz) spectrum | | | Solvent CDCl₃, Chemical shift (δ) |
|---|---|---|---|
| 8.43 | s | 1 H | H2 |
| 6.20 | s | 1 H | H6 |
| 3.94 | s | 3 H | COOCH₃ |
| 2.55–2.70 | m | 1 H | cycloexane CH |
| 1.15–2.15 | m | 10 H | cycloexane CH₂s | e) 5-Cyclohexyl-7-oxo-5-phenyl-7H-thieno[3,2-b]pyran-3-carboxylic acid (Compound 3E)

0.3 mL of 1N sodium hydroxide and 1.0 mL of water were added to a solution of 0.040 g of Compound 3D in 1.8 mL of MeOH and 0.9 mL of 1,4-dioxane at 20–25° C., while stirring. The mixture was heated at 50° C. for 3.5 hours. After cooling to 20–25° C., the mixture was diluted with water and acidified to pH 1 with 3N hydrochloric acid. The precipitated solid was collected by filtration and washed with water to afford 0.028 g (73.5%) of the title compound, melting at 269–275° C.

| ¹H-NMR (200 MHz) spectrum | | | Solvent DMSO-d₆, Chemical shift (δ) |
|---|---|---|---|
| 13.30 | bs | 1 H | COOH |
| 8.78 | s | 1 H | H2 |
| 6.23 | s | 1 H | H6 |
| 2.55–2.70 | m | 1 H | cycloexane CH |
| 1.10–2.05 | m | 10 H | cycloexane CH₂s | f) 5-Cyclohexyl-N-{3-[4-(2-methoxyphenyl)-1-piperazinyl]propyl}-7-oxo-7H-thieno[3,2-b]pyran-3-carboxamide The title compound was prepared as described in Example 2, but substituting Compound 3E for Compound 1G. The crude product was purified by flash chromatography in ethyl acetate:2.7N methanolic ammonia (95:5). The residue, obtained after solvent evaporation from the collected fractions containing the pure title compound (0.03 g; 73%) was dissolved in 5 mL of MeOH and the opalescent solution was clarified with charcoal. Solvent evaporation yielded the pure title compound as a yellow pasty solid (67%).

| ¹H-NMR (200 MHz) spectrum | | | Solvent CDCl₃, Chemical shift (δ) |
|---|---|---|---|
| 8.41 | s | 1 H | H2 |
| 7.15 | 5 | 1 H | NH |
| 6.85–7.10 | m | 4 H | methoxyphenyl Chs |
| 6.21 | s | 1 H | H6 |
| 3.86 | s | 3 H | OCH₃ |
| 3.60 | q | 2 H | NHCH₂ |
| 3.00–3.15 | m | 4 H | 2 piperazine CH₂s |
| 2.55–2.80 | m | 7 H | 2 piperazine CH₂s, cycloexane CH and CH₂CH₂CH₂ |
| 2.05 | dt | 2 H | CH₂CH₂CH₂ |
| 1.20–1.95 | m | 10 H | cycloexane CH₂s |

EXAMPLE 4

N-{3-[4-(2-Methoxyphenyl)-1-piperazinyl]propyl}-7-oxo-5-trifluoromethyl-7H-thieno[3,2-b]pyran-3-carboxamide a) Methyl 7-oxo-5-trifluoromethyl-7H-thieno[3,2-b]pyran-3-carboxylate (Compound 4A)

3.95 mL of trifluoroacetic anhydride and 9.2 mL of 1,8-diazabicyclo[5.4.0]undec-7-ene (DBU) were added to a mixture of 4.10 g of methyl 2-acetyl-3-hydroxythiophene-4-carboxylate and 14 mL of pyridine at 0–5° C. The mixture was heated at 80° C. for 27 hours, during which time a total of 9.9 mL of trifluoroacetic anhydride and a total of 9.2 ml and DBU were added in three additions. The mixture was cooled to 20–25° C., poured into a mixture of ice (250 g) and 37% hydrochloric acid (50 mL), and extracted with ethyl acetate (2×80 mL). The combined organic layers were washed with water, dried over sodium sulphate and evaporated to dryness in vacuo. The residue was taken up with petroleum-ether/ethyl-acetate (7:3) and filtered. The filtrate was purified by flash chromatography using a petroleum ether/ethyl acetate gradient (7:3 to 0:1). The residue was dissolved in diethyl ether, washed with 5% aqueous sodium carbonate and water, dried over sodium sulphate and evaporated to dryness in vacuo to yield the title product (22%) melting at 148–158° C., which could be used in the next step without further purification. The analytical sample was obtained by crystallisation from ethanol. M.p. 163–164° C.

| $^1$H-NMR (200 MHz) spectrum | | Solvent: CDCl$_3$, Chemical shift (δ) | |
|---|---|---|---|
| 8.58 | s | 1 H | H2 |
| 6.80 | s | 1 H | H6 |
| 3.96 | s | 3 H | COOCH$_3$ | b) 7-Oxo-5-trifluoromethyl-7H-thieno[3,2-b]pyran-3-carboxylic acid (Compound 4B)

A mixture of 0.70 g of Compound 4A, 5.6 mL of dioxane and 8.4 mL of 9N hydrochloric acid was stirred at reflux for 75 minutes. After cooling to 20–25° C., the precipitated solid was filtered, washed with dioxane/water 1:1.5 and water to afford 0.46 g of the title compound as a grey solid melting at 249–251° C.

| $^1$H-NMR (200 MHz) spectrum | | Solvent: DMSO-d$_6$, Chemical shift (δ) | |
|---|---|---|---|
| 13.50 | bs | 1 H | COOH |
| 8.25 | s | 1 H | H2 |
| 7.19 | s | 1 H | H6 | c) N-{3-[4-(2-Methoxyphenyl)-1-piperazinyl]propyl}-7-oxo-5-trifluoromethyl-7H-thieno[3,2-b]pyran-3-carboxamide The title compound was prepared as described in Example 2 substituting Compound 4B for Compound 1G. The crude product was purified by flash chromatography in ethyl acetate/2.7N ammonia in methanol (95:5) affording the title compound as a light-brown solid melting at 170–177° C. (33%).

| $^1$H-NMR J(200 MHz) spectrum | | Solvent: CDCl$_3$, Chemical shift (δ) | |
|---|---|---|---|
| 8.55 | s | 1 H | H2 |
| 7.10 | t | 1 H | NH |
| 6.85–7.10 | m | 4 H | methoxyphenyl CHs |
| 6.80 | s | 1 H | H6 |
| 3.88 | s | 3 H | OCH$_3$ |
| 3.60 | l | 2 H | NHCH$_2$ |
| 2.90–3.15 | m | 4 H | 2 piperazine CH$_2$s |
| 2.45–2.80 | m | 6 H | 2 piperazine CH$_2$s, CH$_2$CH$_2$2CH$_2$N |
| 1.88 | dt | 2 H | CH$_2$CH$_2$CH$_2$ |

EXAMPLE 5

7-Oxo-5-phenyl-N-{3-[4-[2-(2,2,2-trifluoroethoxy) phenyl]-1-piperazinyl]propyl}-7H-thieno[3,2-b] pyran-3-carboxamide a) N-(3-Chloropropyl)-7-oxo-5-phenyl-7H-thieno[3,2-b]pyran-3-carboxamide (Compound 5A)

This compound was prepared as described above, in Example 1, with the substitution of 3-chloropropylamine hydrochloride for Compound 1B and doubling the amount of triethylamine used. After dilution with water, the precipitated solid was filtered and, while still on the filter, washed with cold-water:dimethylformamide (2:1) and then with water. The washed solid was suspended in 10% aqueous sodium carbonate, stirred, filtered and washed with water to neutrality. Drying at 70° C. in vacuo yielded the title compound (95%).

| $^1$H-NMR (200 MHz) spectrum | | Solvent: CDCl$_3$, Chemical shift (δ) | |
|---|---|---|---|
| 8.52 | s | 1 H | H2 |
| 7.75–7.85 | m | 2 H | phenyl H2, H6 |
| 7.50–7.60 | m | 3 H | phenyl H3, H4, H5 |
| 7.00 | s | 1 H | NH |
| 6.80 | s | 1 H | H6 |
| 3.65–3.80 | m | 4 H | CH$_2$CH$_2$CH$_2$ |
| 2.15 | dt | 2 H | CH$_2$CH$_2$CH$_2$ | b) 7-Oxo-5-phenyl-N-{3-[4-[2-(2,2,2-trifluoroethoxy) phenyl]-1-piperazinyl]propyl}-7H-thieno[3,2-b]pyran-3-carboxamide A mixture of 0.17 g of Compound 5A, 0.13 g of 1-[2-(2,2,2-trifluoroethoxy)phenyl]-piperazine (prepared as described by EP 0748 800, G. Bantle et al.) and 0.07 g of potassium carbonate was heated at 200° C. for 20 minutes. After cooling to 20–25° C., the crude residue was purified by flash chromatography in ethyl acetate/methanol gradient (95:5 to 9:1) to yield 0.193 g (70%) of the title compound. M.p. 152–158° C.

| $^1$H-NMR (200 MHz) spectrum | | Solvent: CDCl$_3$, Chemical shift (δ) | |
|---|---|---|---|
| 8.45 | s | 1 H | H2 |
| 7.80–7.95 | m | 2 H | phenyl H2, Hy |
| 7.50–7.65 | m | 4 H | CONH, phenyl H3, H4, H5 |
| 6.80 | s | 1 H | H6 |
| 6.75–7.10 | m | 4 H | tribluoroethoxyphenyl CHs |
| 4.44 | q | 2 H | CH$_2$O |
| 3.66 | dt | 2 H | CONHCH$_2$ |
| 2.90–3.05 | m | 4 H | 2 piperazine CH$_2$s |
| 2.50–2.70 | m | 6 H | CH$_2$N and piperazine CH$_2$s |
| 1.80–2.00 | m | 2 H | CH$_2$CH$_2$CH$_2$ |

EXAMPLE 6

N-{3-[4-[2-Methoxy-5-(2,2,2-trifluoroethoxy) phenyl]-1-piperazinyl]propyl}-7-oxo-5-phenyl-7H-thieno[3,2-b]pyran-3-carboxamide a) 1-t-Butoxycarbonyl-4-(5-hydroxy-2-methoxyphenyl) piperazine (Compound 6A)

A solution of 8 g of 1-(5-hydroxy-2-methoxyphenyl) piperazine dihydrobromide and 3.17 g of anhydrous potassium carbonate in 30 mL of water was evaporated to dryness in vacuo. 100 mL of anhydrous tetrahydrofuran and 5.18 g of 97% di-t-butyl dicarbonate (BOC$_2$O) were added to the residue and the mixture was stirred at 20–25° C. for 2 hours, followed by addition of 100 mL of anhydrous tetrahydrofuran. The suspension was filtered and the filtrate evaporated to dryness in vacuo. The residue was dissolved in 200 mL of chloroform. The solution was washed with 5% sodium bicarbonate (3×50 ml) and water (2×50 mL), and dried over sodium sulphate. The solvent was removed at reduced pressure and the residue was purified by flash chromatography in petroleum ether/ethyl acetate (75:25) to yield 1.91 g (28.7%) of Compound 6A and 1.58 g (35.7%) of 1-t-butoxycarbonyl-4-(5-t-butoxycarbonyloxy-2-methoxyphenyl)piperazine. A solution of this by-product in 40 mL of methanol and 6 mL of 1N sodium hydroxide was maintained overnight at 20–25° C. The mixture was neutralized with acetic acid, solvent was removed at reduced pressure and the remaining residue was dissolved in 40 mL of chloroform. After washing with water (3×10 mL) the organic layer was dried over sodium sulphate and the solvent evaporated in vacuo to recover an additional 1.15 g (17.2%) of Compound 6A as a thick oil (total yield 45.9%).

| $^1$H-NMR (200 MHz) spectrum | | | Solvent: CDCl$_3$, Chemical shift (δ) |
|---|---|---|---|
| 6.70 | d | 1 H | H3 of phenyl ring |
| 6.45–6.53 | m | 2 H | H4 and H6 of phenyl ring |
| 5.77 | s | 1 H | OH |
| 3.78 | s | 3 H | CH$_3$O |
| 3.48–3.68 | m | 4 H | 2 piperazine CH$_2$s |
| 2.82–3.05 | m | 4 H | 2 piperazine CH$_2$s |
| 1.48 | 2 | 9 H | (CH$_3$)$_3$C | b) 1-t-Butoxycarbonyl-4-[2-methoxy-5-(2,2,2-trifluoroethoxy)phenyl]piperazine (Compound 6B)

A mixture of 2.83 g of Compound 6A, 6.05 g of cesium carbonate and 2.95 g of 2,2,2-trifluoroethyl p-toluenesulphonate in 60 mL of acetonitrile was refluxed for 16 hours while stirring. The solvent was evaporated off at reduced pressure, 90 mL of brine was added to the residue, and the mixture was extracted with ethyl acetate (3×40 mL). The organic layer was washed with water (3×20 mL) and of brine (20 mL) and dried over sodium sulphate. The solvent was removed at reduced pressure and the residue purified by flash chromatography in a petroleum ether/ethyl acetate gradient (95:5 to 80:20). The solvents were removed in vacuo to yield 1.86 g (52%) of Compound 6B as a white solid. M.p. (98) 102–105° C.

| $^1$H-NMR (200 MHz) spectrum | | | Solvent: CDCl$_3$, Chemical shift (δ) |
|---|---|---|---|
| 6.77 | d | 1 H | H3 of phenyl ring |
| 6.45–6.63 | m | 2 H | H4 and H6 of phenyl ring |
| 4.28 | q | 2 H | CF$_3$CH$_2$O |
| 3.84 | s | 3 H | CH$_3$O |
| 3.53–3.68 | m | 4 H | 2 piperazine CH$_2$s |
| 2.90–3.06 | m | 4 H | 2 piperazine CH$_2$s |
| 1.48 | s | 9 H | (CH$_3$)$_3$C | c) 1-[2-Methoxy-5-(2,2,2-trifluoroethoxy)phenyl]piperazine. 1.9 hydrochloride (Compound of 6C)

A solution of 2.42 mL of trifluoroacetic acid in 30 mL of anhydrous dichloromethane was added dropwise to a solution of 1.17 g of Compound 6B in 40 mL of anhydrous dichloromethane at 3–5° C. while stirring. The mixture was maintained overnight at 20–25° C., washed with 2N sodium hydroxide (2×30 mL) and extracted with 2N hydrochloric acid (3×15 mL). The aqueous acid layer was washed with diethyl ether (2×20 mL) brought to an alkaline pH with 37% sodium hydroxide at 5–10° C., and extracted with diethyl ether (3×30 mL). The organic layer was dried over sodium sulphate and the solvent was removed in vacuo to yield 0.78 g (89%) of compound 6C base as a thick oil. A solution of the compound 6C base in diethyl ether was treated with coal, filtered and acidified by addition of 3.6N HCl in diethyl ether to yield the hydrochloride salt, which was recovered by filtration and crystallized from acetonitrile and ethanol to yield the analytical sample. M.p. (188) 202–208° C. (dec.)

| 1H-NMR (200 MHz) spectrum | | | Solvent: DMSO-d$_6$, Chemical shift (δ) |
|---|---|---|---|
| 9.18 | bs | 2.9 H | NH$_2$$^+$ and NH$^+$ |
| 6.90 | d | 1 H | phenyl H3 |
| 6.67 | dd | 1 H | phenyl H4 |
| 6.59 | d | 1 H | phenyl H6 |
| 4.66 | q | 2 H | CF$_3$CH$_2$O |
| 3.74 | s | 3 H | CH$_3$O |
| 3.18 | bs | 8 H | piperazine CH$_2$s | d) N-{3-[4-[2-Methoxy-5-(2,2,2-trifluoroethoxy)phenyl]-1-piperazinyl]propyl}-7-oxo-5-phenyl-7H-thieno[3,2-b]pyran-3-carboxamide This compound was prepared as described above, in Example 5b, with the exception that Compound 6C was used in place of 1-[2-(2,2,2-trifluoroethoxy)phenyl]piperazine. After cooling to 20–25° C., the crude residue was purified by flash chromatography in ethyl acetate:2N ammonia in methanol (98:2) to yield the title compound (60%). M.p. 156–158° C.

| $^1$H-NMR (200 MHz) spectrum | | | Solvent: CDCl$_3$, Chemical shift (δ) |
|---|---|---|---|
| 8.50 | s | 1 H | H2 |
| 7.80–7.95 | m | 2 H | phenyl H2, H6 |
| 7.40–7.80 | m | 4 H | CONH, phenyl H3, H4, H5 |
| 6.85 | s | 1 H | H6 |
| 6.75 | d | 1 H | trifluoroethoxyphenyl H3 |
| 6.40–6.55 | m | 2 H | trifluoroethoxyphenyl H4, H6 |
| 4.30 | q | 2 H | CH$_2$O |
| 3.80 | s | 3 H | CH$_3$O |
| 3.65 | dt | 2 H | CONHCH$_2$ |
| 2.50–3.10 | m | 10 H | piperazine CH$_2$s and CH$_2$N |
| 1.85–2.10 | m | 2 H | CH$_2$CH$_2$CH$_2$ |

EXAMPLE 7

N-{3-[4-[4-Fluoro-2-(2,2,2-trifluoroethoxy)phenyl]-1-piperazinyl]propyl}-7-oxo-5-phenyl-7H-thieno[3,2-b]pyran-3-carboxamide This compound was prepared as described in Example 5b, with the exception that 1-[4-fluoro-2-(2,2,2-trifluoroethoxy)phenyl]piperazine (prepared as described by G. Bantle et al. in EP 748 800, 1966) was used in place of 1-[2-(2,2,2-trifluoroethoxy)-phenyl]piperazine. After cooling to 20–25° C., the crude residue was purified by flash chromatography in ethyl acetate/2N ammonia in methanol (95:5) to yield the title compound (74%). M.p. 189–191° C.

| $^1$H-NMR (200 MHz) spectrum | | | Solvent: CDCl$_3$, Chemical shift (δ) |
|---|---|---|---|
| 8.45 | s | 1 H | H2 |
| 7.80–7.95 | m | 2 H | Phenyl H2, H6 |
| 7.45–7.65 | m | 4 H | CONH, phenyl H3, H4, H5 |
| 6.80 | s | 1 H | H6 |
| 6.65–6.75 | m | 2 H | trifluoroethoxyphenyl CHs |
| 6.60 | dd | 1 H | trifluoroethoxyphenyl CH |
| 4.35 | q | 2 H | CH$_2$O |
| 3.65 | dt | 2 H | CONHCH$_2$ |
| 2.80–3.00 | m | 4 H | 2 piperazine CH$_2$s |
| 2.50–2.70 | m | 6 H | CH$_2$N and 2 piperazine CH$_2$s |
| 1.90–2.00 | m | 2 H | CH$_2$CH$_2$CH$_2$ |

EXAMPLE 8

Determination of Affinity for Cloned $\alpha_1$ Adrenergic Receptors and 5-HT$_{1A}$ Serotoninergic Receptors by Radioligand Binding Assay Determination of affinity for cloned subtypes of the $\alpha_1$-adrenoceptor was performed in membranes from cells transfected by electroporation with DNA expressing the genes encoding each $\alpha_1$-adrenoceptor subtype.

Cloning and stable expression of the $\alpha_1$-adrenoceptor gene were performed as previously described (Testa et al., Pharmacol. Comm., 6:79–86, 1995 and references). The cell membranes were incubated in 50 nM Tris, pH 7.4, with 0.2 nM [$^3$H]prazosin, in a final volume of 1.02 mL for 30 minutes at 25° C., in the absence or presence of competing drugs (1 pM-10 μM). Non-specific binding was determined in the presence of 10 μM phentolamine. Incubation was stopped by addition of ice-cold Tris buffer and rapid filtration through Schleicher & Schuell GF52 filters that had been pretreated with 0.2%-polyethyleneimine.

Genomic clone G-21 coding for the human 5-HT$_{1A}$-serotoninergic receptor was stably transfected in a human cell line (HeLa) (Fargin et al., J. Biol. Chem., 284:14848–14852, 1989). HeLa cells were grown as monolayers in Dulbecco's modified Eagle's medium (DMEM), supplemented with 10% fetal calf serum and gentamicin (100 μg/mL), at 37° C. in 5% $CO_2$. The cells were detached from the growth flask at 95% confluence by a cell scraper and were lysed in a buffer containing ice cold 5 mM Tris, 5 mM EDTA, (pH 7.4). The homogenates were centrifuged at 40,000×g for 20 minutes and the membranes were resuspended in a small volume of ice-cold buffer containing 5 mM Tris and 5 mM, EDTA (pH 7.4), and immediately frozen and stored at −70° C. until use.

On the day of experiment, the cell membranes were resuspended in a buffer containing 50 mM Tris (pH 7.4), 2.5 mM $MgCl_2$, 10 μM pargyline (Fargin et al., Nature, 335:358–360, 1988). The membranes were incubated in a final volume of 1 mL for 30 minutes at 30° C. with 1.2 nM [$^3$H]8-OH-DPAT, in the absence or presence of test molecules. Non-specific binding was determined in the presence of 10 μM 5-HT. Incubation was stopped by addition of ice-cold Tris buffer and rapid filtration through Schleicher & Schuell GF52 filters that had been pretreated with 0.2%-polyethyleneimine.

Inhibition of specific binding of the radioligands by the test drugs was analyzed to estimate the IC$_{50}$ value by using the non-linear curve-fitting program Allfit (De Lean et al., Am. J. Physiol., 235:E97–E102, 1978).

The IC$_{50}$ value was converted to an affinity constant (Ki) by the equation of Cheng et al., (Biochem. Pharmacol., 22:3099–3108, 1973). Data were expressed as mean of Ki.

RESULTS

The compounds of the invention exhibited the desired potency and selectivity at $\alpha_1$ adrenoceptors, as shown in Table 1.

TABLE 1

Affinity (Ki, nM) of the different compounds tested for recombinant $\alpha_1$-adrenoceptor subtypes and 5-HT$_{1A}$ receptor.

| Example | Human cloned receptors | | | |
|---|---|---|---|---|
| | $\alpha_{1a}$ | $\alpha_{1b}$ | $\alpha_{1d}$ | 5-HT$_{1A}$ |
| 1 | 0.58 | 2.53 | 4.12 | |
| 2 | 0.10 | 7.52 | 2.46 | 4.48 |
| 4 | 0.60 | 23.16 | 3.60 | 26.21 |
| 5 | 0.045 | 4.34 | 1.01 | 7.59 |
| 6 | 3.19 | 39.31 | 48.17 | 1081.00 |
| 7 | 0.17 | 3.47 | 2.45 | 88.54 |

TABLE 1-continued

Affinity (Ki, nM) of the different compounds tested for recombinant $\alpha_1$-adrenoceptor subtypes and 5-HT$_{1A}$ receptor.

| Example | Human cloned receptors | | | |
|---|---|---|---|---|
| | $\alpha_{1a}$ | $\alpha_{1b}$ | $\alpha_{1d}$ | 5-HT$_{1A}$ |
| Compound A | 0.60 | 3.29 | 2.84 | 4.53 |
| Prazosin | 0.61 | 0.42 | 0.23 | >100000 |

EXAMPLE 9

In vitro Evaluation of Functional Antagonism for $\alpha_{1L}$ Adrenoceptors

The functional $\alpha_1$-antagonistic activity of the test compounds against noradrenaline(NA)-induced contractions of rabbit aorta pretreated with chloroethylclonidine ($\alpha_{1L}$ receptor) was evaluated according to the method of Testa et al., (J. Pharmacol. Exp. Ther., 281:1284–1293, 1997). Adult male New Zealand rabbits were sacrificed by cervical dislocation. The aorta was removed, placed in Krebs-Henseleit buffer and dissected free of adhering tissue. Rings were prepared from each artery (8 rings per aorta, about 4–5 mm wide) and suspended in 20 mL organ bath containing Krebs bicarbonate buffer of the following composition: 112 mM NaCl, 5.0 mM KCl, 2.5 mM $CaCl_2$, 1.0 mM $KH_2PO_4$, 1.2 mM $MgSO_4$, 12.0 mM $NaHCO_3$ and 11.1 mM glucose, equilibrated at 37° C. with 95% $O_2$: 5% $CO_2$. Desmethylimipramine (0.1 μM) and corticosterone (1 μM) to block neuronal and extraneuronal uptake of NA, (±)-propranol (1 μM) to block β adrenoceptors and yohimbine (0.1 μM) to block $\alpha_2$ adrenoceptors were added to the buffer. The tissues were subjected to a passive load of 2 g and the tension developed was measured using isometric transducers (Basile 7003).

The preparations were equilibrated for 60 minutes and then primed every 30 minutes with 10 μM NA for three times. The aortic rings were then incubated with the alkylating agent chloroethylclonidine (50 μM) for 30 minutes and then washed extensively three times, over a 30 min period before constructing the NA-concentration/response curve. Following washing, tissue was re-equilibrated for 45 min. Test drug was added and after 30 minutes, a second cumulative-NA-concentration/response curve was constructed. Each antagonist concentration was tested using 2–3 aortic rings from different rabbits.

Dose ratios (i.e., the ratio between the concentrations of noradrenaline required to produce half-maximal response in the presence and in the absence of the test antagonist) were calculated at each concentration of the compounds. The logarithm of these dose ratio −1 was plotted against the logarithm of the compound concentrations (Schild plot) to evaluate the affinity constant Kb.

When only one or two concentrations of the test compounds were utilised, the apparent Kb value was calculated using the formula: Kb=[B]/(DOSE RATIO−1), where B is the antagonist concentration.

RESULTS

The compounds tested showed good affinity for the $\alpha_{1L}$ adrenoceptor subtype. The data are expressed as pKb in Table 2.

TABLE 2

Functional affinity of the tested compounds for the $\alpha_{1L}$ adrenoceptor subtype.

| Example | pKb |
|---|---|
| 1 | 8.17 |
| 2 | 8.85 |
| 4 | 7.92 |
| 5 | 9.12 |
| 7 | 8.66 |
| Comp A | 8.64 |
| Prazosin | 8.11 |

EXAMPLE 10

Effects on Urethral Contractions Induced by Noradrenaline Injection and Blood Pressure in Dogs after Intravenous Administration The experiments were performed according to the method of Imagawa et al (J. Pharmacol. Methods, 22:103–111, 1989), with substantial modifications, as follows: adult male beagle dogs, weighing 8–10 kg, were anaesthetized with pentobarbital sodium (30 mg/kg i.v. and 2 mg/kg/h i.v.), intubated and spontaneously ventilated with room air. In order to monitor systemic blood pressure (BP), a polyethylene (PE) catheter was introduced into the aortic arch through the left femoral artery. A collateral of the left femoral vein was cannulated for infusion of anaesthetic, and the right femoral vein was cannulated for administration of compounds. For intraarterial (i.a.) injection of noradrenaline (NA), a PE catheter was introduced into the lower portion of the abdominal aorta via the right external iliac artery. Through such procedure, NA was selectively distributed to the lower urinary tract. A paramedian vertical suprapubic incision extending from the base of the pelvis to the mid-abdominal region was made and the bladder and the prostate were exposed. The bladder was manually emptied with a syringe. Prostatic urethral pressure was monitored with a Mikro-tip catheter (5F) introduced into the bladder via the external urethral meatus, and withdrawn until the pressure transducer was positioned in the prostatic region of the urethra. A ligature was secured between the neck of the bladder and urethra to isolate the response of the latter and to avoid any interaction with the bladder. Another ligature was put around the Mikro-tip catheter at the external meatus, to secure the catheter itself.

After a stabilizing period following the surgical procedure (30 minutes), in which arterial and prostatic urethral pressures were continuously monitored as basal values, i.a. administration of NA was made at intervals of 20 minutes.

The NA doses were chosen to produce an increase of at least 100% in urethral pressure. The test compounds were administered intravenously in a cumulative manner with intervals of 15–20 minutes between administrations. I.a. injections of NA were repeated 5 minutes after every dosing of test compound with intervals of about 10 minutes between stimulations. In order to compare the effects of the administered compound, dose/response curves (log dose transformation) were constructed by computing, at the peak effect, the percent decrease in diastolic blood pressure and percent inhibition of the increase in urethral pressure induced by NA. Linear regression equations were then used in order to evaluate the theoretical effectiveness as $ED_{25}$ (the effective dose inducing a 25% decrease in diastolic blood pressure) and $ID_{50}$ (the dose inhibiting by 50% the increase in urethral pressure).

RESULTS

The effects obtained after intravenous administration of the compounds of examples 1, 2 and 5 are shown in Table 3. Results obtained after injection of prazosin and Comp A are also shown in the table.

TABLE 3

Data represent the active doses (expressed in µg/kg) inhibiting by 50% the urethral contractions (UC) induced by noradrenaline (NA), the active doses (expressed in µg/kg) in lowering diastolic blood pressure (DBP) and the ratio (DBP/US) between the active doses.

| Compound | UC $ID_{50}$ NA | DBP $ED_{25}$ | Ratio |
|---|---|---|---|
| 1 | 5.3 | 280 | 52.8 |
| 2 | 1.8 | 35.5 | 19.7 |
| 5 | 2.7 | >1000 | >370 |
| Prazosin* | 3.6 | 6.6 | 1.83 |
| Comp A* | 2.4 | 243 | 101.2 |

*Data from Leonardi et al., J. Pharmacol. Exp. Ther. 281:1272–1283, 1997.

The pharmacological results confirm that the compounds of the invention are $\alpha_1$-adrenoceptor antagonists with good selectivity for the $\alpha_1$ adrenoceptor compared to the 5-$HT_{1A}$ receptor, and good affinity also for the $\alpha_{1L}$ subtype, as far as in vitro data are concerned.

The in vivo pharmacological results confirm the high uroselectivity of the compounds of the invention and justify their possible use in the treatment of obstructive diseases of the lower urinary tract, including BPH.

Effective Amounts

The following represent guidelines to effective oral, parenteral or intravenous dose ranges for human hosts, expressed in mg/kg of body weight per day, for use in obstructive disorders of the lower urinary tract:

| General | 0.001–20 |
|---|---|
| Preferred | 0.05–3 |
| Most preferred | 0.5–2 |

The most-preferred values refer to oral dosing. Intravenous dosages should be 10 to 100 fold lower. Selective-use dosages, i.e., dosages that are active in the lower urinary tract without a substantial effect on blood pressure, depend on the particular compound employed. Generally, in the case of a compound selective in inhibiting urethral contraction, up to four times the amount of the $ED_{50}$ used in inhibiting urethral contraction can be administered without substantial effect on blood pressure. Further refinements and optimization of dosages are possible using simple routine experiments. The active compounds of the invention may be orally administered, for example, with an inert diluent or with an edible carrier, or they may be enclosed in gelatine capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but the amount of active ingredient may be varied depending upon the particular form and may conveniently be between 5% and about 70% of the weight of the unit. The amount of active compound in such compositions is such that a suitable dosage will be obtained although the desired dosage can be obtained by administering a plurality of dosage forms. The preferred compositions and preparations according to the invention are prepared so that an oral dosage unit form contains between 1.0–300 milligrams of active compound. The tablets, pills, capsules, troches and the like may also contain, for example, the following ingredients: a binder such as microcrystalline cellulose, gum tragacanth or gelatine; an excipient such as starch or lactose; a disintegrating agent such as alginic acid, sodium starch glycolate, cornstarch and the like; a lubricant such as magnesium stearate or hydrogenated castor oil, a glidant such as colloidal silicon dioxide; a sweetening agent such as sucrose or saccharin; and a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example as coatings. Thus, tablets or pills may be coated with sugar, shellac, or other enteric coating agents. A syrup may contain, in addition to the active compounds, sucrose as a sweetening agent and certain preservatives, dyes, coloring and flavors. The materials used in preparing these various compositions should be pharmaceutically pure and nontoxic in the amounts used. For the purpose of parenteral therapeutic administration, the active compounds of the invention may be incorporated into a solution or suspension. These preparations should contain at least 0.1% of active compound, but it may be varied between 0.5 and about 30% of the weight thereof. The amount of active compound in such compositions is such that a suitable dosage will be obtained. The preferred compositions and preparations according to the present inventions are prepared so that a parenteral dosage unit contains between 0.2 to 100 milligrams of active compound. The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates; citrates or phosphates and agents for the adjustment of tonicity such as sodium chloride or dextrose. The frequency of administration of the present compounds and compositions may be adjusted based on need and physician's advice but will typically be once or twice a day. The parenteral multiple-dose vials may be of glass or plastics material.

Additional compositions suitable for administration by various routes and containing compounds according to the present invention are also within the scope of the invention. Dosage forms, additional ingredients and routes of administration contemplated herein include those disclosed in the United States patents U.S. Pat. No. 4,089,969 to Muchowsk et al. and U.S. Pat. No. 5,091,182 to Ong et al., both incorporated by reference in their entirety.

What is claimed is:

1. A compound having the general formula I

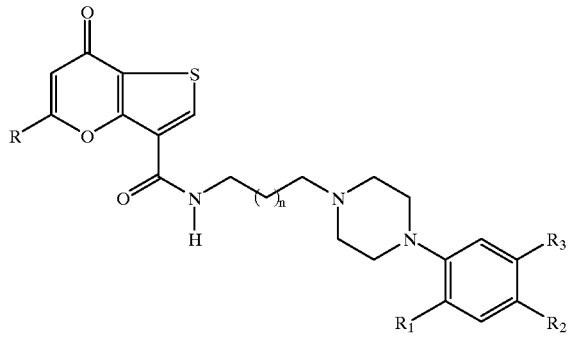

(I)

wherein

R is chosen from the group consisting of an aryl, cycloalkyl, and lower polyhaloalkyl group, $R_1$ is chosen from the group consisting of lower alkyl, lower alkoxy, lower polyfluoroalkoxy, hydroxy and trifluoromethanesulfonyloxy group, each of $R_2$ and $R_3$ being independently chosen from the group consisting of a hydrogen, halogen, lower alkoxy, and lower polyfluoroalkoxy group, and n is 0, 1 or 2, or a piperazine-N-oxide thereof or a pharmaceutically acceptable salt of any of the foregoing.

2. A compound according to claim 1 wherein R is chosen from the group consisting of phenyl, cyclohexyl, and trifluoromethyl group.

3. A compound according to claim 1 wherein $R_1$ is chosen from the group consisting of methyl, methoxy and 2,2,2-trifluoroethoxy group.

4. A compound according to claim 1 wherein $R_2$ is chosen from the group consisting of hydrogen and fluorine.

5. A compound according to claim 1 wherein $R_3$ is chosen from the group consisting of hydrogen, chlorine and a 2,2,2-trifluoroethoxy group.

6. A compound according to claim 1 wherein n=1.

7. A compound selected from the group consisting of a
N-{3-[4-(5-chloro-2-methoxyphenyl)-1-piperazinyl]propyl}-7-oxo-5-phenyl-7H-thieno[3,2-b]pyran-3-carboxamide,
N-{3-[4-(2-methoxyphenyl)-1-piperazinyl]propyl}-7-oxo-5-phenyl-7H-thieno[3,2-b]pyran-3-carboxamide,
5-cyclohexyl-N-{3-[4-(2-methoxyphenyl)-1-piperazinyl]propyl}-7-oxo-7H-thieno[3,2-b]pyran-3-carboxamide,
N-{3-[4-(2-methoxyphenyl)-1-piperazinyl]propyl}-7-oxo-5-trifluoromethyl-7H-thieno[3,2-b]pyran-3-carboxamide,
7-oxo-5-phenyl-N-{3-[4-[2-(2,2,2-trifluoroethoxy)phenyl]-1-piperazinyl]propy}-7H-thieno[3,2-b]pyran-3-carboxamide,
N-{3-[4-[2-methoxy-5-(2,2,2-trifluoroethoxy)phenyl]-1-piperazinyl]propyl}-7-oxo-5-phenyl-7H-thieno[3,2-b]pyran-3-carboxamide, and
N-{3-[4-[4-fluoro-2-(2,2,2-trifluoroethoxy)phenyl]-1-piperazinyl]propyl}-7-oxo-5-phenyl-7H-thieno[3,2-b]pyran-3-carboxamide.

8. A pharmaceutical composition comprising a compound according to any one of claims 1–7 and a pharmaceutically acceptable diluent or carrier.

9. The compound of claim 1 wherein the lower polyhaloalkyl group is a $C_{1-4}$-polyhaloalkyl group.

10. The compound of claim 1 wherein the lower alkyl group is a $C_{1-4}$-alkyl group, the lower alkoxy group is a $C_{1-4}$-alkoxy group, and the lower polyfluoroalkoxy group is a $C_{1-4}$-polyfluoroalkoxy group.

11. The compound of claim 1 wherein the cycloalkyl group is cyclohexyl.

12. A method for preventing or inhibiting contractions of the urethra and lower urinary tract, the method comprising administering a compound according to any one of claims 1–7 to a mammal including humans in need of such treatment in an amount effective for preventing or inhibiting said contractions.

13. A method for preventing or inhibiting contractions of the urethra and lower urinary tract, the method comprising administering a pharmaceutical composition according to claim 8 to a mammal including humans in need of such treatment in an amount effective for preventing or inhibiting said contractions.

14. A method according to claim 12 wherein the administration of said compound causes limited effects on the blood pressure of said mammal including humans.

15. A method according to claim 13 wherein the administration of said compound causes limited effects on the blood pressure of said mammal including humans.

16. A method for the treatment of a patient suffering from benign prostatic hyperplasia, the method comprising administering an effective amount of a compound according to any one of claims 1–7 to a patient in need of such treatment.

17. A method for the treatment of a patient suffering from benign prostatic hyperplasia, the method comprising administering an effective amount of a pharmaceutical composition according to claim 8 to a patient in need of such treatment.

18. A method for reducing lower urinary tract symptoms in a patient, the method comprising administering an effective amount of a compound according to any one of claims 1–7 to a patient in need of such treatment.

19. A method for reducing lower urinary tract symptoms in a patient, the method comprising administering an effective amount of a pharmaceutical composition according to claim 8 to a patient in need of such treatment.

20. The method according to claim 18 wherein said patient is a female.

21. The method according to claim 19 wherein said patient is a female.

22. A method for reducing neurogenic lower urinary tract dysfunction in a patient, the method comprising administering an effective amount of a pharmaceutical composition according to any of claims 1–7 to a patient in need of such treatment.

23. A method for reducing neurogenic lower urinary tract dysfunction in a patient, the method comprising administering an effective amount of a pharmaceutical composition according to claim 8 to a patient in need of such treatment.

* * * * *